United States Patent

Konotsune et al.

[11] Patent Number: 4,508,910
[45] Date of Patent: Apr. 2, 1985

[54] HERBICIDAL 4-BENZOYL-5-HYDROXY-PYRAZALES

[75] Inventors: Takuo Konotsune, Hiromachi; Katsuhiko Kawakubo, Yasumachi, both of Japan

[73] Assignee: Sankyo Company Ltd., Tokyo, Japan

[21] Appl. No.: 199,824

[22] Filed: Oct. 23, 1980

Related U.S. Application Data

[60] Continuation of Ser. No. 953,357, Oct. 23, 1978, abandoned, which is a continuation of Ser. No. 838,083, Sep. 30, 1977, Pat. No. 4,146,726, which is a division of Ser. No. 558,682, Mar. 17, 1975, Pat. No. 4,063,925.

[30] Foreign Application Priority Data

Mar. 28, 1974 [JP] Japan .................. 49-34939

[51] Int. Cl.$^3$ .................. A01N 43/56; C07D 231/20
[52] U.S. Cl. .................. 548/367; 71/92
[58] Field of Search .................. 548/367; 71/92

[56] References Cited

U.S. PATENT DOCUMENTS 4,008,200  2/1977  Avar et al. .................. 548/367
4,146,540  3/1979  Avar et al. .................. 548/105

OTHER PUBLICATIONS

Sarenko et al., Khim Geterotsikl. Soedin., 1972, 6, pp. 799–808.

Primary Examiner—Henry R. Jiles
Assistant Examiner—Kurt G. Briscoe
Attorney, Agent, or Firm—Toren, McGeady and Stanger

[57] ABSTRACT

Herbicidally active compound having the formula

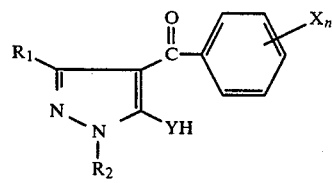

wherein
$R_1$ represents hydrogen atom or a lower alkyl group,
$R_2$ represents a lower alkyl group or a lower alkenyl group,
X represents a variety of substituents of the phenyl ring, and
Y represents oxygen or sulfur, and
the salts and organic acid esters thereof.

3 Claims, No Drawings

HERBICIDAL 4-BENZOYL-5-HYDROXY-PYRAZALES

This is a continuation of application Ser. No. 953,357, filed on Oct. 23, 1978, now abandoned, which, in turn, is a continuation of application Ser. No. 838,083, U.S. Pat. No. 4,146,726, filed Sept. 30, 1977, which, in turn, is a division of application Ser. No. 558,682, U.S. Pat. No. 4,063,925, filed Mar. 17, 1975.

This invention relates to the use of pyrazole derivatives as a herbicide and also to a certain group of new pyrazole derivatives.

More particularly, it is concerned with a herbicidal composition which comprises as an active ingredient a compound having the formula

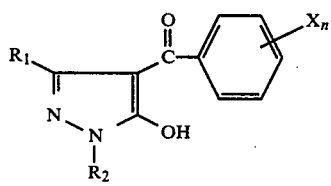
(I)

(wherein $R_1$ represents hydrogen atom or a lower alkyl group, $R_2$ represents a lower alkyl group or a lower alkenyl group, X represents a halogen atom, nitro group, a lower alkyl group, a halogenated lower alkyl group, a lower alkoxy group, a lower alkanesulfonyl group, cyano group, a lower alkylthio group or an aliphatic acyl group and n is an integer of 1 to 4 and when n is 2, 3 or 4, X's may be the same or different), a salt thereof or an organic acid ester thereof, and an agriculturally acceptable carrier, with a method for the destruction of undesirable weeds which comprises applying to said weeds a herbicidal amount of the compound having the above formula (I), as well as with some new pyrazole derivatives having the formula

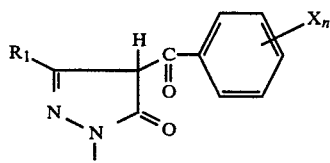
(II)

(wherein $R_1$ represents hydrogen atom or a lower alkyl group, $R_2$ represents a lower alkyl group or a lower alkenyl group, Z represents a halogen atom, nitro group, a lower alkyl group, a halogenated lower alkyl group, a lower alkoxy group, a lower alkanesulfonyl group, cyano group, a lower alkylthio group, an aliphatic acyl group or benzoyl group, n is an integer of 1 to 4, when n is 2, 3 or 4, Z's may be the same or different and Y represents oxygen atom or sulfur atom; provided that those wherein $R_1$ and $R_2$ are methyl groups, Z is chlorine atom at 2-position, n is 1 and Y is oxygen atom and wherein $R_1$ and $R_2$ are methyl groups, Z is nitro group at 4-position, n is 1 and Y is oxygen atom are excluded.

The compounds of the above-mentioned formula (I) may be present in the form of the tautomerism as shown under.

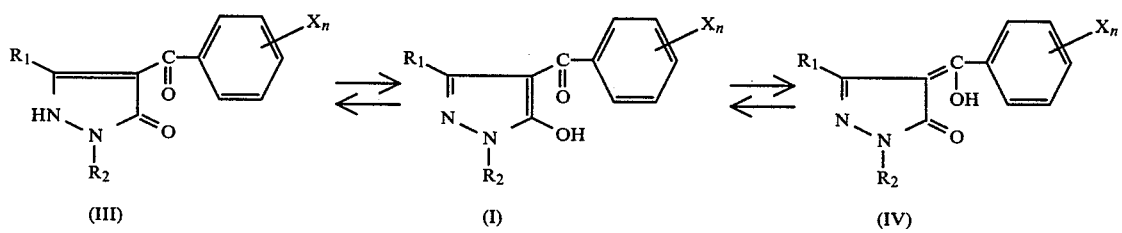

(wherein $R_1$, $R_2$, X, and n have the same meanings as above). It is, of course, to be noted that the same tautomerism as shown above may be observed with respect to the compounds (II).

In the above-mentioned formula (I), $R_1$ is preferably hydrogen atom; a straight or branched lower alkyl group having 1 to 6 carbon atoms, particularly 1 to 3 carbon atoms, methyl, ethyl, n-propyl, isopropyl, n-butyl, isobutyl, sec-butyl, tert-butyl, n-pentyl, isopentyl, sec-amyl, 2-methylbutyl, tert-amyl, n-hexyl, 2-hexyl, 2-methylpentyl, 3-methylpentyl, 4-methylpentyl, 3-hexyl, 2-ethylbutyl, 2-methyl-2-pentyl or 2,2-dimethylbutyl. $R_2$ preferably is a straght or branched lower alkyl group having 1 to 6 carbon atoms, particularly 1 to 3 carbon atoms, as exemplified with regard to $R_1$ and a straight or branched lower alkenyl group having 3 to 6 carbon atoms, particularly 3 or 4 carbon atoms such as allyl, 2-butenyl, 1-methyl-2-propenyl, 2-methyl-2-propenyl, 1-methyl-2-butenyl, 2-methyl-2-butenyl, 3- butenyl, 1-methyl-3-butenyl, 2-methyl-3-butenyl, 3-methyl-2-butenyl, 3-pentenyl, 2-hexenyl, 3-hexenyl or 4-hexenyl. X is preferably a halogen atom such as chlorine, bromine, fluorine or iodine; nitro group; a straight or branched lower alkyl group having 1 to 4 carbon atoms such as methyl, ethyl, n-propyl, isopropyl, n-butyl, isobutyl or tert.-butyl, particularly methyl group; a lower alkyl group having 1 to 2 carbon atoms and substituted with 1 to 3 halogen atoms such as trifluoromethyl, 2,2,2-trichloroethyl, 2,2-dibromoethyl 2,2,2-tribromoethyl, 2-iodoethyl or 2,2-diiodoethyl; a straight or branched lower alkoxy group having 1 to 4 carbon atoms such as methoxy, ethoxy, n-propoxy, isopropoxy, n-butoxy or isobutoxy, particularly methoxy group; a straight or branched lower alkanesulfonyl group having 1 to 4 carbon atoms such as methanesulfonyl, ethanesulfonyl, 1-propanesulfonyl, 2-propanesulfonyl, 1-butanesulfonyl or 2-butanesulfonyl, particularly methanesulfonyl group; cyano group; a straight or branched lower alkylthio group having 1 to 4 carbon atoms such as methylthio, ethylthio, n-propylthio, isopropylthio, n-butylthio or isobutylthio; an aliphatic acyl group such as a straight or branched lower alkanoyl group having 2 to 5 carbon atoms such as acetyl, propionyl, butyryl or pivaloyl.

The salts of the compounds of the above-mentioned formula (I) include the salts with monovalent to trivalent metallic ions such as sodium, potassium, calcium, magnesium, aluminum, iron, manganese, zinc, nickel, cobalt or copper; the salts with complex ions such as $[Cu(H_2O)_2]^{++}$, $[Mn(H_2O)_2]^{++}$, $[Ni(H_2O)_4]^{++}$, $[A(OH)]^{++}$, $[Zn(OH)]^+$, $[Cu(OH)]^+$, $[Cu(NH_3)_2]^{++}$ or $[Co(NH_2CH_2CH_2NH_2)]^{++}$; the salts with ammonium ion such as $N^+H_4$, $N^+H(CH_3)_3$, $N^+H_2(C_2H_5)_2$, $N^+H_3CH(CH_3)_2$, $N^+H_3CH_2CH_2OH$ or $N^+H_3CH_2CH_2OC_2H_5$; the salts with mineral acids such as hydrochloric acid, sulfuric acid, nitric acid or hydrobromic acid.

The organic acid esters of the compounds of the above-mentioned formula (I) may be esters of those organic acids that are capable of forming the corresponding esters at the 5-position in the pyrazole ring and also converting to the original compounds (I) by decomposition upon application. These organic acids are contemplated to include (1) an aliphatic, alicyclic or aromatic carboxylic acid of the formula

R$_3$COOH wherein R$_3$ is a straight or branched alkyl group having 1 to 17 carbon atoms such as methyl, ethyl, n-propyl, isopropyl, n-butyl, isobutyl, tert.-butyl, heptyl, undecyl, tetradecyl or heptadecyl; a lower alkyl group having 1 to 4 carbon atoms, particularly 1 to 2 carbon atoms, and substituted with 1 to 4 halogen atoms such as chloromethyl, bromomethyl, iodomethyl, 2,2,2-trichloroethyl, 2,2-dibromoethyl, 2,2,2-tribromoethyl, 2-iodoethyl, 2,2-diiodoethyl, or 1,1,2,2-tetrafluoroethyl; a straight or branched alkenyl group having 2-17 carbon atoms, particularly 3-5 carbon atoms, such as vinyl, isopropenyl, allyl, 1-methyl-2-propenyl, 2-methyl-2-propenyl, 2-butenyl, 1-methyl-2-butenyl, 2-methyl-2-butenyl, 3-butenyl, 1-methyl-3-butenyl, 2-methyl-3-butenyl, 2-heptenyl, 2-undecenyl, 2-tetradecenyl, 2-heptadecenyl, 3-heptadecenyl or 8,11-heptadecadienyl; a 5- to 7-membered cycloalkyl group such as cyclopentyl, cyclohexyl or cycloheptyl; a phenyl group which may have 1 to 3 substituents of nitro, halogen and/or alkyl of 1 to 4 carbon atoms, particularly 1 carbon atom, such as phenyl, 2-nitrophenyl, 4-nitrophenyl, 2-tolyl, 3-tolyl, 4-tolyl, 2-chlorophenyl, 4-chlorophenyl, 2-bromophenyl, 4-bromophenyl, 2,4-dichlorophenyl, 2,4,6-trichlorophenyl or 2-chloro-4-nitrophenyl; a phenylalkyl group which may have 1–3 of nitro and/or halogen as substituents in the phenyl moiety and has 1–5 carbon atoms, particularly 1 or 2 carbon atoms such as benzyl, phenethyl, phenylpropyl, phenylbutyl, phenylpentyl, 4-nitrobenzyl, 4-nitrophenethyl, 2-chlorobenzyl, 4-chlorophenethyl, 2-bromobenzyl, 4-bromophenethyl, 3-(2,4-dichlorophenyl)propyl or 4-(2,4,6-trichlorophenyl)butyl; styryl group; or a phenoxyalkyl group which may have 1 or 2 of halogen and/or methyl as substituents in the phenyl moiety and has 1 to 3 carbon atoms, (2) a carbamic acid of the formula

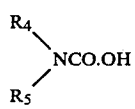

$$\begin{array}{c} R_4 \\ \phantom{R}\diagdown \\ \phantom{RRR}NCO.OH \\ \phantom{R}\diagup \\ R_5 \end{array}$$

wherein R$_4$ and R$_5$ individually represent a straight or branched lower alkyl group having 1–4 carbon atoms such as methyl, ethyl, n-propyl, isopropyl, n-butyl or isobutyl or R$_4$ and R$_5$ jointly represent pentamethylene group, (3) a sulfonic acid of the formula

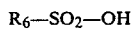

R$_6$—SO$_2$—OH wherein R$_6$ represents a straight or branched lower alkyl group having 1–4 carbon atoms such as methyl, ethyl, n-propyl, n-butyl or isobutyl; a lower alkyl group substituted with 1–3 halogens and having 1–3 carbon atoms, particularly 1 or 2 carbon atoms such as chloromethyl, bromomethyl, iodomethyl, trifluoromethyl, 1-chloroethyl, 1-bromoethyl or 1,1-dichloroethyl; or a phenyl group which may have straight or branched alkyl of 1–12 carbon atoms particularly 1 or 2 carbon atoms, e.g., methyl, ethyl, n-propyl, isopropyl, n-butyl, isobutyl or dodecyl or halogen, e.g., chloro as substituents, (4) a diester of thiophosphoric acid of the formula

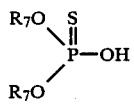

$$\begin{array}{c} R_7O \phantom{aa} S \\ \phantom{RR}\diagdown \phantom{a} \| \\ \phantom{RRRRR} P—OH \\ \phantom{R}\diagup \\ R_7O \end{array}$$

wherein R$_7$'s may be the same or different and represent a straight or branched lower alkyl group having 1–4 carbon atoms such as methyl, ethyl, n-propyl, isopropyl, n-butyl or isobutyl, (5) a monoester of carbonic or thiocarbonic acid of the formula

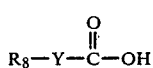

$$R_8—Y—\overset{\overset{\displaystyle O}{\|}}{C}—OH$$

wherein R$_8$ represents a straight or branched lower alkyl group having 1–4 carbon atoms such as methyl, ethyl, n-propyl, isopropyl, n-butyl, isobutyl or sec.-butyl; phenyl group; oor a phenylalkyl group which may have as substituents 1–3 of nitro and/or halogen in the phenyl moiety and has 1 or 2 carbon atoms in the alkyl moiety such as benzyl, phenethyl, 4-nitrobenzyl, 2-chlorobenzyl, 4-chlorophenethyl, 2-bromobenzyl, 2,4-dichlorobenzyl or 2,4,6-trichlorobenzyl and Y represents oxygen atom or sulfur atom, (6) a dibasic acid of the formula

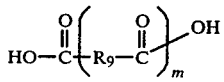

wherein m is 0 or 1, $R_9$ is an alkylene group having 1 to 10 carbon atoms such as methylene, ethylene, trimethylene, tetramethylene, octamethylene or decamethylene; vinylene group; or o-, m- or p-phenylene group or both C=O may be linked without $R_9$ and, when m is zero, only the dibasic acid

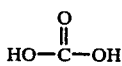

being included within the scope of this formula, and (7) a 3-oxo-4-isoxazolin-2-yl carboxylic acid of the formula

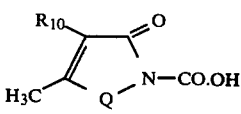

wherein $R_{10}$ is hydrogen atom or a halogen atom.

In agricultural chemicals field, there were previously proposed various types of compounds as a herbicide and many of them have been nowadays practically utilized as an active ingredient in herbicidal compositions. However, there is a continuous demand for much more effective herbicidal compounds in the art.

As a result of our earnest studies on pyrazole ring-containing substances and their herbicidal activities, we have found that the pyrazole derivatives having the above formula (I), the salts thereof and the organic acid esters thereof show prominent herbicidal activities and also that the pyrazole derivatives having the above for formula (II) are new substances which have also herbicidal activities.

With respect the prior art found during the above-mentioned our studying, it is pointed out that only 4-benzoyl-5-hydroxy-1,3-dimethylpyrazole and its utility as a chelating agent are disclosed in Chemische Berichte, 106, 332–338 (1973) and also that synthesis of 1,3-dimethyl-4-(2-chlorobenzoyl)-5-hydroxypyrazole and 1,3-dimethyl-4-(4-nitrobenzoyl)-5-hydroxypyrazole is briefly disclosed without any indication of their property, use, usage etc. in "The Chemistry of Heterocyclic Compounds" (Russian origin, 1972, No. 6, 799–804).

Accordingly, it is a primary object of this invention to provide an effective herbicidal composition containing a pyrazole derivative (I).

Another object of this invention is to provide a certain group of new pyrazole derivatives (II) having herbicidal activities.

Other objects and advantages of this invention will become apparent from the description given hereinbelow.

In one aspect of this invention, there is provided a herbicidal composition which comprises as an active ingredient a pyrazole compound of the above formula (I), a salt thereof or an organic acid ester thereof and an agriculturally acceptable carrier.

Of the compounds having the above formula (I), preferable are those wherein $R_1$ is hydrogen atom or an alkyl group of 1–6 carbon atoms, $R_2$ is an alkyl group of 1–6 carbon atoms or an alkenyl group of 3–6 carbon atoms, X is a halogen atom, nitro group, an alkyl group of 1–4 carbon atoms, a halogenated alkyl group of 1–2 carbon atoms and having 1–3 halogen atoms, an alkoxy group of 1–4 carbon atoms, an alkanesulfonyl group of 1–4 carbon atoms, cyano group, an alkylthio group of 1–4 carbon atoms, an alkanoyl group of 2–5 carbon atoms or an aliphatic acyl group of 2–5 carbon atoms and n is an integer of 1–3 and when n is 2 or 3, X's may be the same or different.

A more preferable group of the compounds having the above formula (I) includes those wherein $R_1$ is hydrogen atom or an alkyl group of 1–3 carbon atoms, $R_2$ is an alkyl group of 1–3 carbon atoms or an alkenyl group of 3 or 4 carbon atoms, X is a halogen atom, cyano group, nitro group, an alkyl group of 1–4 carbon atoms, an alkoxy group of 1–4 carbon atoms, an alkanesulfonyl group of 1–4 carbon atoms or trifluoromethyl group and n is an integer of 1–3 and when n is 2 or 3, X's may be the same or different.

A most preferable group of the compounds having the above formula (I) includes those wherein $R_1$ is methyl group, $R_2$ is methyl group or allyl group, X is chlorine atom, nitro group, cyano group, methyl group, methoxy group, methanesulfonyl group or trifluoromethyl group and n is an integer of 1–3 and when n is 2 or 3, X's may be the same or different, in view of their herbicidal activities.

Salts and organic acid esters of the compounds (I) may be advantageously employed as an active ingredient in the present composition. Particularly preferable salts are those metal salts, ammonium salt and mineral acid salts as set forth above. Organic acids for particularly preferable organic acid esters are those aliphatic, alicyclic or aromatic carboxylic acids, sulfonic acid, carbonic acid or thiocarbonic acid monoester and dibasic acids as set forth above.

More preferable organic acids are the carboxylic acid having the above formula wherein $R_3$ is a halogenoalkyl group of 1–2 carbon atoms and of 1–4 halogen atoms, an alkenyl group of 3–5 carbon atoms, a 5- or 6-membered cycloalkyl group, a phenyl group optionally having 1–3 substituents of nitro, halogen and/or methyl, a phenylalkyl group of 1 or 2 carbon atoms in the alkyl moiety and optionally having 1–3 substituents of nitro and/or halogen in the phenyl moiety or a phenoxyalkyl group of 1 or 2 carbon atoms in the alkyl moiety and optionally having 1 or 2 substituents of halogen and/or nitro; the sulfonic acids having the above formula wherein $R_6$ is an alkyl group of 1–3 carbon atoms, a halogenoalkyl group of 1 or 2 carbon atoms and 1–3 halogen atoms or a phenyl group optionally having $C_1$ or $C_2$ alkyl or halogen;

the monoesters of carbonic or thiocarbonic acid having the above formula wherein $R_8$ is an alkyl group of 1–4 carbon atoms, phenyl group or a phenylalkyl group of 1 or 2 carbon atoms in the alkyl moiety and optionally having 1 or 2 substituents of nitro and/or halogen in the phenyl moiety; and the dibasic acids having the above formula wherein $R_9$ is an alkylene group of 1–3 carbon atoms and m is zero or 1.

The compounds having the above-mentioned formula (I) which may be employed in the present herbicidal composition are illustratively exemplified as hereunder (Compound No. will be frequently referred to hereinbelow).

| Compound No. | Compound |
|---|---|
| 1. | 1,3-dimethyl-4-(3-chlorobenzoyl)-5-hydroxypyrazole |
| 2. | 1,3-dimethyl-4-(4-chlorobenzoyl)-5-hydroxypyrazole |
| 3. | 1,3-dimethyl-4-(2-chlorobenzoyl)-5-hydroxypyrazole |
| 4. | 1,3-dimethyl-4-(3,4-dichlorobenzoyl)-5-hydroxypyrazole |
| 5. | 1,3-dimethyl-4-(4-methylbenzoyl)-5-hydroxypyrazole |
| 6. | 1,3-dimethyl-4-(3-methylbenzoyl)-5-hydroxypyrazole |
| 7. | 1,3-dimethyl-4-(3-trifluoromethylbenzoyl)-5-hydroxypyrazole |
| 8. | 1,3-dimethyl-4-(2-methoxybenzoyl)-5-hydroxypyrazole |
| 9. | 1,3-dimethyl-4-(4-nitrobenzoyl)-5-hydroxypyrazole |
| 10. | 1,3-dimethyl-4-(3-nitrobenzoyl)-5-hydroxypyrazole |
| 11. | 1,3-dimethyl-4-(2,4-dichlorobenzoyl)-5-hydroxypyrazole |
| 12 | 1,3-dimethyl-4-(3,5-dinitrobenzoyl)-5-hydroxypyrazole |
| 13. | 1,3-dimethyl-4-(4-bromobenzoyl)-5-hydroxypyrazole |
| 14. | 1,3-dimethyl-4-(2-nitro-4-chlorobenzoyl)-5-hydroxypyrazole |
| 15. | 1,3-dimethyl-4-(3,5-dichlorobenzoyl)-5-hydroxypyrazole |
| 16. | 1,3-dimethyl-4-(2-chlorobenzoyl)-5-methoxycarbonyloxypyrazole |
| 17. | 1,3-dimethyl-4-(2-chlorobenzoyl)-5-(N,N—dimethylcarbamoyloxy)pyrazole |
| 18. | 1,3-dimethyl-4-(2-chlorobenzoyl)-5-acetoxypyrazole |
| 19. | 1,3-dimethyl-4-(2-nitrobenzoyl)-5-hydroxypyrazole |
| 20. | 1,3-dimethyl-4-(3,4,5-trimethoxybenzoyl)-5-hydroxypyrazole |
| 21. | 1,3-dimethyl-4-(2-fluorobenzoyl)-5-hydroxypyrazole |
| 22. | 1,3-dimethyl-4-(2-bromobenzoyl)-5-hydroxypyrazole |
| 23. | 1,3-dimethyl-4-(2,5-dichlorobenzoyl)-5-hydroxypyrazole |
| 24. | 1,3-dimethyl-4-(4-methoxybenzoyl)-5-hydroxypyrazole |
| 25. | 1,3-dimethyl-4-(4-methylthiobenzoyl)-5-hydroxypyrazole |
| 26. | 1,3-dimethyl-4-(3,4-dimethoxybenzoyl)-5-hydroxypyrazole |
| 27. | 1,3-dimethyl-4-(4-tert.-butylbenzoyl)-5-hydroxypyrazole |
| 28. | 1,3-dimethyl-4-(3,4-dimethylbenzoyl)-5-hydroxypyrazole |
| 29. | 1,3-dimethyl-4-(3,5-dimethylbenzoyl)-5-hydroxypyrazole |
| 30. | bis[1,3-dimethyl-4-(2,4-dichlorobenzoyl)-5-pyrazolyl]sebacate |
| 31. | bis[1,3-dimethyl-4-(2,4-dichlorobenzoyl)-5-pyrazolyl]maleate |
| 32. | 1,3-dimethyl-4-(2-chloro-4-nitrobenzoyl)-5-hydroxypyrazole |
| 33. | 1,3-dimethyl-4-(2,4-dichlorobenzoyl)-5-(4-methylbenzoyloxy)pyrazole |
| 34. | 1-methyl-3-n-propyl-4-(2-chlorobenzoyl)-5-hydroxypyrazole |
| 35. | 1-methyl-4-(2-chlorobenzoyl)-5-hydroxypyrazole |
| 36. | 1,3-dimethyl-4-(3,5-dimethoxybenzoyl)-5-hydroxypyrazole |
| 37. | 1-methyl-3-ethyl-4-(2,4-dichlorobenzoyl)-5-hydroxypyrazole |
| 38. | 1,3-dimethyl-4-(2-nitro-5-methylbenzoyl)-5-hydroxypyrazole |
| 39. | 1,3-dimethyl-4-(4-methanesulfonylbenzoyl)-5-hydroxypyrazole |
| 40. | 1-isopropyl-3-methyl-4-(2-chlorobenzoyl)-5-hydroxypyrazole |
| 41. | 1,3-dimethyl-4-(2-iodobenzoyl)-5-hydroxypyrazole |
| 42. | 1,3-dimethyl-4-(4-fluorobenzoyl)-5-hydroxypyrazole |
| 43. | 1,3-dimethyl-4-(4-cyanobenzoyl)-5-hydroxypyrazole |
| 44. | 1-ethyl-3-methyl-4-(2,4-dichlorobenzoyl)-5-hydroxypyrazole |
| 45. | 1,3-dimethyl-4-(2,4-dichlorobenzoyl)-5-lauroyloxypyrazole |
| 46. | 1,3-dimethyl-4-(2,4-dichlorobenzoyl)-5-stearoyloxypyrazole |
| 47. | 1,3-dimethyl-4-(2,4-dichlorobenzoyl)-5-crotonyloxypyrazole |
| 48. | 1,3-dimethyl-4-(2,4-dichlorobenzoyl)-5-benzoyloxypyrazole |
| 49. | 1,3-dimethyl-4-(2,4-dichlorobenzoyl)-5-pyrazolyl methanesulfonate |
| 50. | 1,3-dimethyl-4-(2-chloro-4-cyanobenzoyl)-5-hydroxypyrazole |
| 51. | 1,3-dimethyl-4-(2,4-dichlorobenzoyl)-5-pyrazolyl 4-toluenesulfonate |
| 52. | 1,3-dimethyl-4-(2-acetylbenzoyl)-5-hydroxypyrazole |
| 53. | 1,3-dimethyl-4-(2,4,5-trichlorobenzoyl)-5-hydroxypyrazole |
| 54. | 1,3-dimethyl-4-(2,3,4,5-tetrachlorobenzoyl)-5-hydroxypyrazole |
| 55. | bis[1,3-dimethyl-4-(2-chloro-4-nitrobenzoyl)-5-pyrazolyl]terephthalate |
| 56. | 1,3-dimethyl-4-(2,4-dichlorobenzoyl)-5-acetoxypyrazole |
| 57. | 1,3-dimethyl-4-(2,4-dichlorobenzoyl)-5-propionyloxypyrazole |
| 58. | 1,3-dimethyl-4-(2,4-dichlorobenzoyl)-5-isobutyryloxypyrazole |
| 59. | 1,3-dimethyl-4-(2,4-dichlorobenzoyl)-5-(5-methyl-3-oxo-4-isoxazolin-2-ylcarbonyloxy)pyrazole |
| 60. | 1,3-dimethyl-4-(2,4-dichlorobenzoyl)-5-(3-oxo-4-chloro-5-methyl-4-isoxazolin-2-ylcarbonyloxy)-pyrazole |
| 61. | 1,3-dimethyl-4-(2,4-dichlorobenzoyl)-5-hydroxypyrazole hydrochloride |
| 62. | 1,3-dimethyl-4-(2,3-dichloro-4-nitrobenzoyl)-5-hydroxypyrazole |
| 63. | 1,3-dimethyl-4-(2,4-dichlorobenzoyl)-5-methoxycarbonyloxypyrazole |
| 64. | 1,3-dimethyl-4-(2,4-dichlorobenzoyl)-5-n-propoxycarbonyloxypyrazole |
| 65. | 1,3-dimethyl-4-(2,4-dichlorobenzoyl)-5-benzyloxycarbonyloxypyrazole |
| 66. | bis[1,3-dimethyl-4-(2,4-dichlorobenzoyl)-5-pyrazolyl]carbonate |
| 67. | 1,3-dimethyl-4-(2,4-dichlorobenzoyl)-5-hydroxypyrazole calcium salt |
| 68. | 1,3-dimethyl-4-(2,4-dichlorobenzoyl)-5-hydroxypyrazole magnesium salt |
| 69. | 1,3-dimethyl-4-(2,4-dichlorobenzoyl)-5-hydroxypyrazole isopropylamine salt |
| 70. | 1,3-dimethyl-4-(2,4-dichloro-5-methylbenzoyl)-5-hydroxypyrazole |
| 71. | 1,3-dimethyl-4-(3,4-dimethoxybenzoyl)-5-hydroxypyrazole hydrochloride |
| 72. | 1,3-dimethyl-4-(2,4-dichlorobenzoyl)-5-phenoxycarbonyloxypyrazole |
| 73. | 1,3-dimethyl-4-(2,4-dichlorobenzoyl)-5-linoleyloxypyrazole |
| 74. | 1,3-dimethyl-4-(2,4-dichlorobenzoyl)-5-chloroacetoxypyrazole |
| 75. | 1,3-dimethyl-4-(2,4-dichlorobenzoyl)-5-(2-methyl-4-chlorophenoxyacetoxy)pyrazole |
| 76. | 1,3-dimethyl-4-(2-chloro-4-nitrobenzoyl)-5-benzoyloxypyrazole |
| 77. | 1,3-dimethyl-4-(2-chloro-4-nitrobenzoyl)- |

| Compound No. | Compound |
|---|---|
| | 5-(4-chlorobenzoyloxy)pyrazole |
| 78. | 1,3-dimethyl-4-(2-chloro-4-nitrobenzoyl)-5-(2-chloro-4-nitrobenzoyloxy)pyrazole |
| 79. | 1,3-dimethyl-4-(2-chloro-4-nitrobenzoyl)-5-cinnamoyloxypyrazole |
| 80. | bis[1,3-dimethyl-4-(2-chloro-4-nitrobenzoyl)-5-pyrazolyl]succinate |
| 81. | 1,3-dimethyl-4-(2-chloro-4-nitrobenzoyl)-5-acetoxypyrazole |
| 82. | 1,3-dimethyl-4-(2-chloro-4-nitrobenzoyl)-5-pivaloyloxypyrazole |
| 83. | 1,3-dimethyl-4-(2,4-dichlorobenzoyl)-5-pivaloyloxypyrazole |
| 84. | 1,3-dimethyl-4-(2,4-dichlorobenzoyl)-5-phenylthiocarbonyloxypyrazole |
| 85. | 1,3-dimethyl-4-(2,4-dichlorobenzoyl)-5-n-butylthiocarbonyloxypyrazole |
| 86. | 1,3-dimethyl-4-(2,4-dichlorobenzoyl)-5-phenylacetoxypyrazole |
| 87. | 1,3-dimethyl-4-(2,4-dichlorobenzoyl)-5-(4-chlorophenylacetoxy)pyrazole |
| 88. | 1,3-dimethyl-4-(3-methyl-4-nitrobenzoyl)-5-hydroxypyrazole |
| 89. | 1,3-dimethyl-4-(2-chloro-4-nitro-5-methylbenzoyl)-5-hydroxypyrazole |
| 90. | 1,3-dimethyl-4-(2-methylbenzoyl)-5-hydroxypyrazole |
| 91. | 1,3-dimethyl-4-(2,4-dimethylbenzoyl)-5-hydroxypyrazole |
| 92. | 1,3-dimethyl-4-(2,6-dichlorobenzoyl)-5-hydroxypyrazole |
| 93. | 1,3-dimethyl-4-(2,4-dichlorobenzoyl)-5-pyrazolyl 4-chlorobenzenesulfonate |
| 94. | 1,3-dimethyl-4-(4-nitrobenzoyl)-5-acetoxypyrazole |
| 95. | 1,3-dimethyl-4-(2,4-dichlorobenzoyl)-5-cyclohexylcarbonyloxypyrazole |
| 96. | 1,3-dimethyl-4-(2,4-dichlorobenzoyl)-5-(2,4-dichlorophenoxyacetoxy)pyrazole |
| 97. | 1,3-dimethyl-4-(2,4-dichlorobenzoyl)-5-(2,4-dichlorobenzoyloxy)pyrazole |
| 98. | O,O-diethyl O-[1,3-dimethyl-4-(2-chlorobenzoyl)-5-pyrazoyl]phosphorothioate |
| 99. | 1,3-dimethyl-4-(2,4-dichlorobenzoyl)-5-pyrazolyl chloromethanesulfonate |
| 100. | 1,3-dimethyl-4-(2,4-dichlorobenzoyl)-5-hydroxypyrazole aluminum salt |
| 101. | 1,3-dimethyl-4-(2,4-dichlorobenzoyl)-5-hydroxypyrazole iron salt |
| 102. | 1,3-dimethyl-4-(2,4-dichlorobenzoyl)-5-hydroxypyrazole copper salt |
| 103. | 1,3-dimethyl-4-(2,4-dichlorobenzoyl)-5-hydroxypyrazole sodium salt |
| 104. | 1,3-dimethyl-4-(2,4-dichlorobenzoyl)-5-pyrazolyl benzenesulfonate |
| 105. | 1,3-dimethyl-4-(2-nitro-4-chlorobenzoyl)-5-pyrazolyl 4-toluenesulfonate |
| 106. | 1,3-dimethyl-4-(2-nitro-4-chlorobenzoyl)-5-pyrazolyl benzenesulfonate |
| 107. | 1-ethyl-3-methyl-4-(2,4-dichlorobenzoyl)-5-pyrazolyl 4-toluenesulfonate |
| 108. | 1-ethyl-3-methyl-4-(2-nitro-4-chlorobenzoyl)-5-hydroxypyrazole |
| 109. | 1-ethyl-3-methyl-4-(2-nitro-4-chlorobenzoyl)-5-pyrazolyl 4-toluenesulfonate |
| 110. | 1,3-dimethyl-4-(2-chlorobenzoyl)-5-pyrazolyl methanesulfonate |
| 111. | 1,3-dimethyl-4-(2,4-dichlorobenzoyl)-5-ethylthiocarbonyloxypyrazole |
| 112. | 1,3-dimethyl-4-(2,4-dichlorobenzoyl)-5-benzylthiocarbonyloxypyrazole |
| 113. | 1-allyl-3-methyl-4-(4-chlorobenzoyl)-5-hydroxypyrazole |
| 114. | 1-allyl-3-methyl-4-(2-chlorobenzoyl)-5-hydroxypyrazole |
| 115. | 1-allyl-3-methyl-4-(2,4-dichlorobenzoyl)-5-(4-chlorobenzoyloxy)pyrazole |
| 116. | 1-(2-hexenyl)-3-methyl-4-(4-bromobenzoyl)-5-hydroxypyrazole |
| 117. | 1-(3-methyl-2-butenyl)-3-methyl-4-(2-nitro-4-chlorobenzoyl)-5-hydroxypyrazole |
| 118. | 1-(3-pentenyl)-3-methyl-4-(2-chlorobenzoyl)-5-methoxycarbonyloxypyrazole |
| 119. | 1-allyl-3-methyl-4-(2-chlorobenzoyl)-5-(N,N—dimethylcarbamoyloxy)pyrazole |
| 120. | 1-allyl-3-methyl-4-(2-chlorobenzoyl)-5-acetoxypyrazole |
| 121. | 1-(2-methyl-2-propenyl)-3-methyl-4-(2-fluorobenzoyl)-5-hydroxypyrazole |
| 122. | 1-(2-butenyl)-3-methyl-4-(2-bromobenzoyl)-5-hydroxypyrazole |
| 123. | bis[1-allyl-3-methyl-4-(2,4-dichlorobenzoyl)-5-pyrazol]sebacate |
| 124. | bis[1-allyl-3-methyl-4-(2,4-dichlorobenzoyl)-5-pyrazolyl]maleate |
| 125. | 1-allyl-3-methyl-4-(2-chloro-4-nitrobenzoyl)-5-pyrazolyl-4-toluenesulfonate |
| 126. | 1-allyl-3-methyl-4-(2,4-dichlorobenzoyl)-5-(4-methylbenzoyloxy)pyrazole |
| 127. | 1-allyl-4-(2-chlorobenzoyl)-5-hydroxypyrazole |
| 128. | 1-allyl-3-ethyl-4-(2-chlorobenzoyl)-5-hydroxypyrazole |
| 129. | 1-(2-butenyl)-3-methyl-4-(2-iodobenzoyl)-5-hydroxypyrazole |
| 130. | 1-(1-methyl-2-butenyl)-3-methyl-4-(4-fluorobenzoyl)-5-hydroxypyrazole |
| 131. | 1-(2-butenyl)-3-methyl-4-(2,4-dichlorobenzoyl)-5-hydroxypyrazole |
| 132. | 1-allyl-3-methyl-4-(2,4-dichlorobenzoyl)-5-lauroyloxypyrazole |
| 133. | 1-allyl-3-n-propyl-4-(2,4-dichlorobenzoyl)-5-benzoyloxypyrazole |
| 134. | 1-allyl-3-methyl-4-(2,4-dichlorobenzoyl)-5-pyrazolyl methanesulfonate |
| 135. | 1-allyl-3-methyl-4-(2,4-dichlorobenzoyl)-5-pyrazolyl 4-toluenesulfonate |
| 136. | 1-(2-butenyl)-3-methyl-4-(2,4,5-trichlorobenzoyl)-5-hydroxypyrazole |
| 137. | 1-allyl-3-methyl-4-(2,3,4,5-tetrachlorobenzoyl)-5-hydroxypyrazole |
| 138. | 1-allyl-3-methyl-4-(2,4-dichlorobenzoyl)-5-(4-nitrobenzyloxycarbonyloxy)pyrazole |
| 139. | bis[1-allyl-3-methyl-4-(2-chloro-4-nitrobenzoyl)-5-pyrazolyl]terephthalate |
| 140. | 1-allyl-3-methyl-4-(2,4-dichlorobenzoyl)-5-propionyloxypyrazole |
| 141. | 1-allyl-3-methyl-4-(2,4-dichlorobenzoyl)-5-isobutylyloxypyrazole |
| 142. | 1-(2-methyl-2-propenyl)-3-methyl-4-(2,4-dichlorobenzoyl)-5-(5-methyl-3-oxo-4-isoxazolin-2-ylcarbonyloxy)pyrazole |
| 143. | 1-allyl-3-methyl-4-(2,4-dichlorobenzoyl)-5-(3-oxo-4-chloro-5-methyl-4-isoxazolin-2-ylcarbonyloxy)pyrazole |
| 144. | 1-allyl-3-methyl-4-(2,4-dichlorobenzoyl)-5-hydroxypyrazole hydrochloride |
| 145. | 1-allyl-3-methyl-4-(2,4-dichlorobenzoyl)-5-methoxycarbonyloxypyrazole |
| 146. | 1-allyl-3-methyl-4-(2,4-dichlorobenzoyl)-5-n-propoxycarbonyloxypyrazole |
| 147. | 1-allyl-3-methyl-4-(2,4-dichlorobenzoyl)-5-benzyloxycarbonyloxypyrazole |
| 148. | bis[1-allyl-3-methyl-4-(2,4-dichlorobenzoyl)-5-pyrazolyl]carbonate |
| 149. | 1-allyl-3-methyl-4-(2,4-dichlorobenzoyl)-5-hydroxypyrazole calcium salt |
| 150. | 1-(2-methyl-2-propenyl)-3-methyl-4-(2,4-dichlorobenzoyl)-5-hydroxypyrazole magnesium salt |
| 151. | 1-allyl-3-methyl-4-(2,4-dichlorobenzoyl)-5-hydroxypyrazole isopropylamine salt |
| 152. | 1-allyl-3-methyl-4-(2,4-dichlorobenzoyl)-5-linoleyloxypyrazole |
| 153. | 1-allyl-3-methyl-4-(2,4-dichlorobenzoyl)-5-chloroacetoxypyrazole |
| 154. | 1-allyl-3-methyl-4-(2,4-dichlorobenzoyl)-5-(2-methyl-4-chlorophenoxyacetoxy)pyrazole |
| 155. | 1-(2-methyl-2-propenyl)-3-methyl-4-(2-chloro-4-nitrobenzoyl)-5-benzoyloxypyrazole |
| 156. | 1-allyl-3-methyl-4-(2-chloro-4-nitrobenzoyl)-5-(4-chlorobenzoyloxy)pyrazole |

| Compound No. | Compound |
|---|---|
| 157. | 1-allyl-3-methyl-4-(2-chloro-4-nitrobenzoyl)-5-cinnamoyloxypyrazole |
| 158. | bis[1-allyl-3-methyl-4-(2-chloro-4-nitrobenzoyl)-5-pyrazolyl]succinate |
| 159. | 1-allyl-3-methyl-4-(2-chloro-4-nitrobenzoyl)-5-pivaloyloxypyrazole |
| 160. | 1-allyl-3-methyl-4-(2,4-dichlorobenzoyl)-5-pivaloyloxypyrazole |
| 161. | 1-(2-methyl-2-propenyl)-3-methyl-4-(2,4-dichlorobenzoyl)-5-phenylthiocarbonyloxypyrazole |
| 162. | 1-allyl-3-methyl-4-(2,4-dichlorobenzoyl)-5-n-butylthiocarbonyloxypyrazole |
| 163. | 1-allyl-3-methyl-4-(2,4-dichlorobenzoyl)-5-phenylacetoxypyrazole |
| 164. | 1-allyl-3-methyl-4-(2,4-dichlorobenzoyl)-5-(4-chlorophenylacetoxy)pyrazole |
| 165. | 1-allyl-3-methyl-4-(2,6-dichlorobenzoyl)-5-hydroxypyrazole |
| 166. | 1-allyl-3-methyl-4-(2,4-dichlorobenzoyl)-5-pyrazolyl 4-chlorobenzenesulfonate |
| 167. | 1-(1-methyl-2-propenyl)-3-methyl-4-(4-nitrobenzoyl)-5-acetoxypyrazole |
| 168. | 1-(2-butenyl)-3-methyl-4-(2,4-dichlorobenzoyl)-5-(2,4-dichlorobenzoyloxy)pyrazole |
| 169. | O,O-diethyl[O-1-allyl-3-methyl-4-(2-chlorobenzoyl)-5-pyrazolyl]phosphorothioate |
| 170. | 1-allyl-3-methyl-4-(2,4-dichlorobenzoyl)-5-pyrazolyl chloromethanesulfonate |
| 171. | 1-allyl-3-methyl-4-(2,4-dichlorobenzoyl)-5-hydroxypyrazole aluminum salt |
| 172. | 1-(2-methyl-2-propenyl)-3-methyl-4-(2,4-dichlorobenzoyl)-5-hydroxypyrazole iron salt |
| 173. | 1-allyl-3-methyl-4-(2,4-dichlorobenzoyl)-5-hydroxypyrazole copper salt |
| 174. | 1-allyl-3-methyl-4-(2,4-dichlorobenzoyl)-5-hydroxypyrazole sodium salt |
| 175. | 1-allyl-3-methyl-4-(2,4-dichlorobenzoyl)-5-pyrazolyl benzenesulfonate |
| 176. | 1-allyl-3-methyl-4-(2-nitro-4-chlorobenzoyl)-5-pyrazolyl 4-toluenesulfonate |
| 177. | 1-(2-butenyl)-3-methyl-4-(2-nitro-4-chlorobenzoyl)-5-pyrazolyl benzenesulfonate |
| 178. | 1-allyl-3-methyl-4-(2-nitro-4-chlorobenzoyl)-5-hydroxypyrazole |
| 179. | 1-allyl-4-(2-nitro-4-chlorobenzoyl)-5-pyrazolyl 4-toluenesulfonate |
| 180. | 1-(2-hexenyl)-3-methyl-4-(2-chlorobenzoyl)-5-pyrazolyl methanesulfonate |
| 181. | 1-allyl-3-methyl-4-(2,4-dichlorobenzoyl)-5-ethylthiocarbonyloxypyrazole |
| 182. | 1-allyl-3-methyl-4-(2,4-dichlorobenzoyl)-5-benzylthiocarbonyloxypyrazole |
| 183. | 1-allyl-3-methyl-4-(2,4-dichlorobenzoyl)-5-hydroxypyrazole |
| 184. | 1-allyl-3-methyl-4-(3-chlorobenzoyl)-5-stearoyloxypyrazole |
| 185. | 1-(3-butenyl)-3-methyl-4-(3,4-dichlorobenzoyl)-5-crotonyloxypyrazole |
| 186. | 1-allyl-3-methyl-4-(3-nitrobenzoyl)-5-hydroxypyrazole |
| 187. | 1-allyl-3-methyl-4-(3,5-dinitrobenzoyl)-5-phenoxycarbonyloxypyrazole |
| 188. | 1-allyl-3-methyl-4-(4-bromobenzoyl)-5-(2-chloro-4-nitrobenzoyloxy)pyrazole |
| 189. | 1-(3-butenyl)-3-methyl-4-(3,5-dichlorobenzoyl)-5-hydroxypyrazole |
| 190. | 1-allyl-3-methyl-4-(2-nitrobenzoyl)-5-pyrazolyl 4-toluenesulfonate |
| 191. | 1-allyl-3-methyl-4-(2,5-dichlorobenzoyl)-5-(2,4-dichlorophenoxyacetoxy)pyrazole |
| 192. | 1-allyl-3-methyl-4-(2,3-dichloro-4-nitrobenzoyl)-5-cyclohexylcarbonyloxypyrazole |

Of the above-illustrated pyrazole compounds, may be mentioned as a preferable class those compounds having the Compound Nos. 11, 14, 19, 22, 23, 26, 32, 33, 35, 38, 39, 41, 44, 45, 46, 47, 48, 49, 51, 56, 57, 58, 59, 60, 61, 63, 64, 65, 67, 68, 69, 72, 73, 74, 80, 83, 84, 85, 86, 90, 96, 97, 100, 101, 102, 103, 104, 105, 106, 107, 108, 109, 111, 125, 141 and 183.

The compounds having the above formula (I), salts thereof and organic acid esters thereof can be readily prepared, for example, by the following processes. (Process A) The 5-hydroxypyrazole derivatives (I) can be easily prepared by reacting the 5-pyrazolone derivatives (VI) with the acyl halides (VII) in the presence of a catalyst as shown by the following equation.

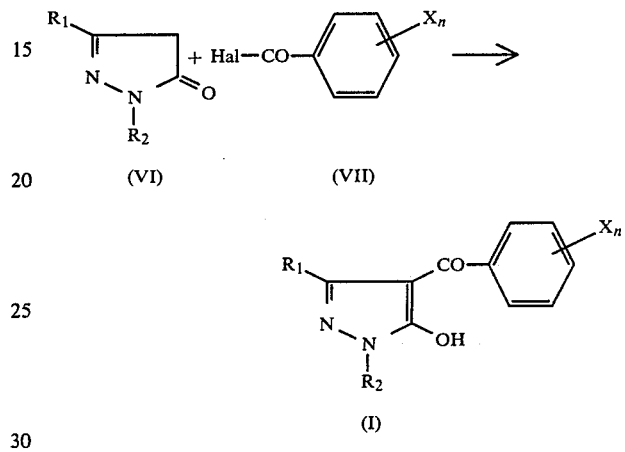

(wherein $R_1$, $R_2$, X and n have the same meanings as above and Hal means a halogen atom.)

The above reaction may be preferably effected in the presence of a solvent. As the solvent employable, any solvent may be used without particular limitation if it could not participate in the reaction and there may be mentioned, for instance, ethers or mixtures thereof such as diethylether, tetrahydrofuran, diethylether-dioxane, tetrahydrofuran-dioxane; halogenated hydrocarbons such as dichloromethane, carbon tetrachloride; secondary or tertiary alcohols such as isopropanol, isobutanol, tert.butanol; and the like. In particular, ethers and secondary alcohols are preferably employed. The reaction may also be preferably effected in the presence of a catalyst. As the catalyst to be used are mentioned alkaline earth metal hydroxides such as calcium hydroxide. In particular, calcium hydroxide is preferably used. The amount of a catalyst to be employed is preferably 1-2 moles per mole of the starting material (VI). The reaction temperature is not particularly critical and the reaction may be effected at room temperature or a reflux temperature of the solvent employed. Particularly, the reaction may be preferably conducted at a reflux temperature of the solvent employed. The reaction period may vary mainly upon the reaction temperature and the sort of the reagent employed, but it is usually within a range of about 1 to 10 hours. And, the acyl halides which may be employed in the above-mentioned reaction may be, for example, acid chlorides or acid bromides.

After completion of the reaction, the desired compounds may be recovered from the reaction mixture by a conventional method. And, the starting materials of the formula (VI) are prepared according to the method disclosed in Chemische Berichte, 43, 2106 (1910).

(Process B) The compounds having the formula (I) are obtainable by heating the corresponding 5- halogenopyrazole derivatives (VIII) with alkali metal hydrosulfides such as sodium hydrosulfide or alkali metal hydroxides such as sodium hydroxide or potassium hydroxide.

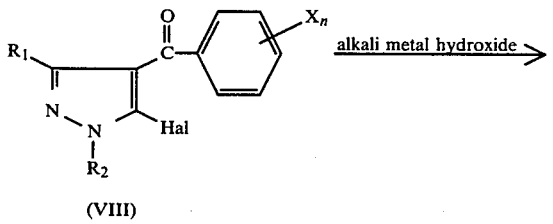

(VIII)

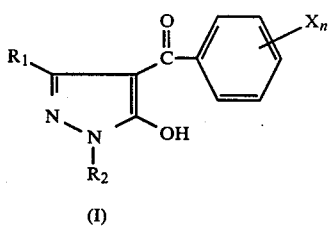

(I)

(wherein $R_1$, $R_2$, X, and n have the same meanings as above.)

In the above-mentioned reaction, water may be employed as a solvent. And, a mixture of water with an organic solvent may be used and, as examples of such organic solvents, may be mentioned ethers such as tetrahydrofuran, dioxane; alcohols such as methanol, ethanol. The reaction temperature is not particularly critical and the reaction may be effected at room temperature or a reflux temperature of the solvent and, particularly, it can be preferably effected at a temperature around the reflux temperature of the solvent. The reaction period may vary mainly upon the reaction temperature and the sort of the reagent employed, but usually about 1 to 10 hours. And, the starting materials of the formula (VIII) are prepared according to the method disclosed in Chemische Berichte, 50, 737 (1917) and United Kingdom Patent Specification No. 1268608.

(Process C) The organic acid esters of the compounds having the formula (I) are easily prepared by reacting the compounds of the formula (I) with an acylating agent as shown in the following schema.

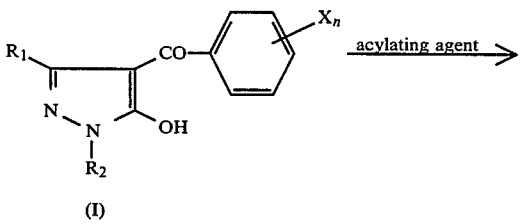

(I)

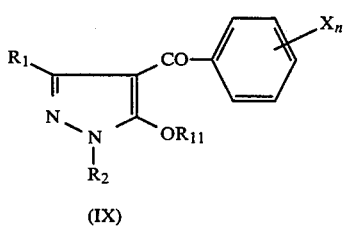

(IX)

(wherein $R_1$, $R_2$, X, and n have the same meanings as above and $R_{11}$ represents a residue of an organic acid.)

The above-mentioned reaction may be preferably effected in the presence of a solvent. As the solvent which may be employed, there is no particular limitation thereon if it does not participate in the present reaction and, for example, ethers or mixtures thereof such as diethyl ether, tetrahydrofuran, diethyl etherdioxane, tetrahydrofurandioxane; aromatic hydrocarbons such as benzene, toluene, xylene; halogenated hydrocarbons such as dichloromethane, chloroform, carbon tetrachloride and, in particular, the aromatic hydrocarbons and ethers are preferably employed. And, the acylating agents which may be employed are acyl halides such as acid chlorides and acid bromides; carboxylic acids in the presence of carbodiimides such as 1,3-dicyclohexylcarbodiimide; or acid anhydrides and acid chlorides are preferable and the reaction is effected in the presence of an acid binding agent. The reaction temperature is not particularly critical and the reaction is usually conducted at room temperature to a reflux temperature of the solvent. The reaction period may very mainly upon the reaction temperature, the sort of the reagent etc., but usually about 1-24 hours.

(Process D) The salts of the compound having the formula (I) with a metallic ion, a complex ion and ammonium ion are formed by adjusting a pH of a solution of the compound of the formula (I) to not less than about 3 in the presence of a cation. As the solvent which may be used for the formation of the above-mentioned salts, there is no particular limitation and, for instance, are preferably employed water; alcohols such as methanol or ethanol; ethers such as tetrahydrofuran or dioxane; aromatic hydrocarbons such as benzene; halogenated hydrocarbons such as dichloromethane or chloroform or mixture of these organic solvents with water. Depending upon changes in cation valency and solvent, various salts having different coordinate proportions of the compound having the formula (I) and the cation of 1:1, 1:2, 1:3 and the like are formed.

(Process E) The salts of the compound having the formula (I) and a mineral acid are easily prepared by mixing the compound having the formula (I) with the mineral acid in a suitable solvent. As the solvent which may be used, there is no particular limitation and there may be preferably mentioned, for instance, water; alcohols such as methanol or ethanol; ethers such as tetrahydrofuran or dioxane; aromatic hydrocarbons such as benzene; halogenated hydrocarbons such as dichloromethane or chloroform; or mixtures of these organic solvent and water. In general, the salts with the mineral acid are formed at a pH not more than about 3 of the solution.

The compounds of the above-mentioned formula (I), salts thereof and organic acid esters thereof are utilized as herbicides and have a property of killing weeds by causing chlorosis.

In a paddy field, particularly prominent herbicidal effects against perennial weeds such as those of the family Cyperaceae, for example, "Hotarui" (*Scirpus hotarui* Ohwi.), "Mizugayatsuri" (*Cyperus serotinus* Rottb.) and the like and those of the family Alismataceae, for example, "Omodaka" (*Sagittaria trifolia* L.), "Urikawa" (*Sagittaria pygmaea* Miq.), which are difficult to be controlled by usual herbicides, can be achieved by pre- and post-emergency treatment in soil without any harmful effect on transplanted rice plants and growing rice plants and, furthermore, monocotyledonous weeds such as those of the family Gramineae, for example, barnyardgrass, panic grass and the like and broad-leaf weeds such as those of the family Scrophulariaceae, for example, false pimpernel, "Murasakisagigoke" (*Mazus miquelii* Makino), "Abunome" (*Dopatrium junceum* Hamilt.) and the like, those of the family Cruciferae, for example, wavy bittercress, marsh yellow cress, "Mizutagarashi" (*Cardamine lyrate* Bunge) and the like, those of the family Lythraceae, for example, toothcup, "Mizumatsuba" (*Rotala mexicana* Cham.) and the like and those of the family Compositae, for example, ragwort, American false daisy and the like.

In an upland field, pre- and post-emergency treatment in soils shows particularly prominent effect against weeds of the family Caryophyllaceae, for example, common chickweed, Bog stichwort, mouse-ear chickweed, pearlwort and the like and, furthermore, broad-leaf weeds such as those of the family Portulacaceae, for example, common purslane and the like, those of the family Amaranthaceae, for example, pigweed, rough pigweed and the like, those of the family Chenopodiaceae, for example, "Akaza" (*Chenopodium album* L.), common lamb's-quarters, "Koakaza" (*C. ficifolium* Smith) and the like, those of the family Commelinaceae, for example, asatic dayflower and the like, those of the family Labiatae, for example, henbit, "Kiranso" (*Ajuga decumbens* Thunb.) and the like, those of the family Oxalidaceae, for example, creeping wood sorrel, violet wood sorrel and the like, those of the family Leguminosae, for example, "Nekohagi" (*Lespedeza pilosa* Seib et Zucc.), hairy vetch, common vetch and the like, those of the family Euphorbiaceae, for example, Virginia coperleaf, milk purslane and the like can be effectively controlled. And, narrow-leaf weeds, in particular, those of the family Cyperaceae, such as "Kayatsurigusa" (*Cyperus microiria* Steud.) and the like are effectively controlled and those of the family Gramineae such as wheatgrass, crab-grass, "Komehishiba" (*Digitaria timorensis* Balansa), barnyardgrass, green foxtail, "Akinoenokorogusa" (*Setaria Faberi* Herrmann), foxtail and the like are also effectively controlled. On the other hand, crops such as rice plants, corns, sugar beets, soybeans, cotton plants, radishes, tomatoes, carrots, Chinese cabbages, lettuces and the like do not suffer from phytotoxicity.

Additionally, the compounds having the above-mentioned formula (I) are effectively usable as herbicides in an orchard, a non-crop land, a forest and so on.

The compounds in this invention may be formulated for use to the preparations commonly employed as a herbicide, for example, powdery dusts, coarse dusts, fine granules, granules, wettable powders, emulsifiable concentrates, aqueous liquids, water soluble powders, oil suspensions and so on, with admixture of a carrier and, if required, other auxilliary agents. The carrier as used herein means a synthetic or natural and inorganic or organic substance that is mixed with on active compound and can assist an active compound in its arrival to the portion to be treated and make it easy to store, transport or handle.

As suitable solid carriers may be mentioned inorganic substances such as clays, which may be represented by Kaolinite, Montmorillonite or Attapulgite, talc, mica, pyrophyllite, pumice, vermiculite, gypsum, calcium carbonate, dolomite, diatomaceous earth, magnesium carbonate, apatite, zeolite, silicic anhydride, synthetic calcium silicate and the like, vegetable organic substances such as soybean meal, tobacco powder, walnut powder, wheat flour, wood meal, starch, crystalline cellulose and the like, synthetic or natural high polymer compounds such as cumarone resin, petroleum resin, alkyd resin, polyvinyl chloride, polyalkylene glycol, ketone resin, ester gum, copal gum, dammar gum, and the like, waxes such as carnauba wax, beeswax and the like or urea.

As suitable liquid media or carriers may be mentioned paraffin or naphthene hydrocarbons such as kerosine, mineral oil, spindle oil, white oil and the like, aromatic hydrocarbons such as benzene, toluene, xylene, ethylbenzene, cumene, methylnaphthalene and the like, chlorinated hydrocarbons such as carbon tetrachloride, chloroform, trichloroethylene, monochlorobenzene, o-chlorotoluene and the like, ethers such as dioxane, tetrahydrofuran and the like, ketones such as acetone, methylethylketone, diisobutylketone, cyclohexanone, acetophenone, isophorone and the like, esters such as ethyl acetate, amyl acetate, ethylene glycol acetate, diethylene glycol acetate, dibutyl maleate, diethyl succinate and the like, alcohols such as methanol, n-hexanol, ethylene glycol, diethylene glycol, cyclohexanol, benzyl alcohol and the like, ether alcohols such as ethylene glycol ethyl ether, ethylene glycol phenyl ether, diethylene glycol ethyl ether, diethylene glycol butyl ether and the like, polar solvents such as dimethylformamide, dimethylsulfoxide and the like or water.

As the surface active agents used for emulsifying, dispersing, wetting, spreading, binding, controlling disintegration, stabilizing active ingredient, improving fruidity, rust proofing and so on may be utilized any of non-ionic, anionic, cationic and amphoteric ones, but non-ionic and/or anionic agents are usually employed. As suitable non-ionic surface active agents may be mentioned, for example, polymerization adducts of ethylene oxide to higher alcohols such as lauryl alcohol, stearyl alcohol, oleyl alcohol and the like, polymerization adducts of ethylene oxide to alkyl phenols such as isooctyl phenol, nonyl phenol and the like, polymerization adducts of ethylene oxide to alkyl naphthols such as butyl naphthol, octyl naphthol and the like, polymerization adducts of ethylene oxide to higher fatty acids such as palmitic acid, stearic acid, oleic acid and the like, polymerization adducts of ethylene oxide to mono- or dialkyl phosphoric acids such as stearyl phosphoric acid, dilauryl phosphoric acid and the like, polymerization adducts of ethylene oxide to amines such as dodecyl amine, stearic acid amide and the like, polymerization adducts of ethylene oxide to higher fatty acid esters of polyhydric alcohols such as sorbitan and said fatty acid esters, polymerization adducts of ethylene oxide to propylene oxide and so on. As suitable anionic surface active agents may be mentioned, for example, alkyl sulfate salts such as sodium lauryl sulfate, oleyl sulfate amine salt and the like, alkyl sulfonate salts such as sodium dioctyl sulfosuccinate, sodium 2-ethylhexene sulfonates and the like, aryl sulfonate salts such as sodium isopropylnaphthalene sulfonate, sodium methylenebisnaphthalene sulfonate, sodium ligninsulfonate, sodium dodecylbenzene sulfonate and the like.

Moreover, the herbicidal compositions of this invention may be used in combination with high molecular compounds or other auxiliary agents such as casein, gelatin, albmin, glue, sodium alginate, carboxymethyl cellulose, methyl cellulose, hydroxyethyl cellulose, polyvinyl alcohol and the like for improving properties and increasing biological effects thereof.

The above-mentioned carriers and various auxiliary agents may be optionally utilized alone or in combination therewith for desired purposes, with consideration for the type of a preparation, application and other factors.

In general, the herbicidal composition of this invention may contain the active compound (I) in an amount of 0.1–99% by weight, based upon the composition.

Dusts usually contain, for example, 1 to 25 parts by weight of the active compound and the remainder is a solid carrier.

Wettable powders usually contain, for example, 25–90 parts by weight of the active compound and the remainder is a solid carrier and a dispersing and wetting agent, if required, together with a protective colloidal agent, a thixotropic agent, an anti-foaming agent and the like.

Granules usually contain 1–35 parts by weight of the active compound and a major portion of the remainder is a solid carrier. The active compound is homogeneously admixed with the solid carrier or adhered or adsorbed on the carrier surface and the size of a granule is about 0.2–1.5 mm.

Emulsifiable concentrates usually contain, for example, 5–50 parts by weight of the active compound and about 5–20 parts by weight of an emulsifying agent, the remainder being a liquid carrier, if required, together with a corrosive inhibitor.

The herbicidal compositions of this invention, which are formulated into various types of preparations as above, may be applied in a paddy or upland field at 10–2000 g, preferably 100–500 g of the active ingredient per 10 a. for pre- or post-emergency soil treatment to control weeds effectively. Also, weeds can be unselectively controlled in non-crop land such as road, ground, house site, railroad and the like, at an application rate of the active ingredient of 200–4000 g per 10 a.

The herbicidal compositions of this invention may be preferably combined with other herbicides for broader herbicidal spectra and, in some cases, a synergistic effect is expectable. As examples of such other herbicides may be mentioned, for instance, triazine type herbicides such as 2-methylthio-4,6-bisethylamino-1,3,5-triazine; 2-chloro-4,6-bisethylamino-1,3,5-triazine; 2-methoxy-4-ethylamino-6-isopropylamino-1,3,5-triazine; 2-chloro-4-ethylamino-6-isopropylamino-s-triazine; 2-methylthio-4,6-bis(isopropylamino)-s-triazine; 2-methylthio-4-ethylamino-6-isopropylamino-s-triazine and the like, phenoxy type herbicides such as 2,4-dichlorophenoxyacetic acid and its methyl, ethyl or butyl ester; 2-chloro-4-methylphenoxyacetic acid; 4-chloro-2-methylphenoxyacetic acid, ethyl 2-methyl-4-chlorophenoxybutyrate and the like, diphenyl ether type herbicides such as 2,4,6-trichlorophenyl-4'-nitrophenyl ether; 2,4-dichlorophenyl-4'-nitrophenyl ether; 3,5-dimethylphenyl-4'-nitrophenyl ether and the like, urea type herbicides such as 3-(3,4-dichlorophenyl)-1-methoxy-1-methylurea; 3-(3,4-dichlorophenyl)-1,1-dimethylurea; 3-(4-chlorophenyl)-1,1-dimethylurea and the like, carbamate type herbicides such as 3-methoxycarbonylaminophenyl-N-(3-methylphenyl)carbamate; isopropyl N-(3-chlorophenyl)carbamate; methyl N-(3,4-dichlorophenyl)carbamate and the like, uracil type herbicides such as 5-bromo-3-sec-butyl-6-methyluracil; 1-cyclohexyl-3,5-propyleneuracil and the like, thiolcarbamate type herbicides such as S-(4-chlorobenzyl)-N,N-diethylthiolcarbamate; S-ethyl N-cyclohexyl-N-ethylthiol carbamate; S-ethyl-hexahydro-1H-azepine-1-carbothioate; S-ethyl-N,N-di-n-propylthiocarbamate and the like, pyridinium salt type herbicides such as 1,1'-dimethyl-4,4'-bispyridinium dichloride and the like, phosphorus type herbicides such as N-(phosphonomethyl)glycine and the like, aniline type herbicides such as α,α,α-trifluoro-2,6-dinitro-N,N-dipropyl-p-toluidine; 4-(methylsulfonyl)-2,6-dinitro-N,N-dipropylaniline and the like, acid anilide type herbicides such as 2-chloro-2',6'-diethyl-N-(butoxymethyl)acetanilide; 2-chloro-2',6'-diethyl-N-(methoxymethyl)acetanilide; 3,4-dichloropropionanilide and the like, 5-tert-butyl-3-(2,4-dichloro-5-isopropoxyphenyl)1,3,4-oxadiazolin-2-one; 2-[N-isopropyl-N-(4-chlorophenyl)-carbamoyl]-4-chloro-5-methyl-4-isoxazolin-3-one; 3-isopropylbenzo-2-thia-1,3-diazinon-(4)-2,2-dioxide; 3-(2-methylphenoxy)pyridazine and the like, but they are not critical.

The herbicidal compositions of this invention may be also applied with admixture of plant growth regulators such as sodium naphthyl acetate; 1,2-dihydropyridazine-3,6-dione; gibberellins and the like, fungicides such as methyl 1-(butylcarbamoyl)-2-benzimidazolecarbamate; 1,2-bis(3-methoxycarbonyl-2-thioureido)benzene; 3-hydroxy-5-methylisoxazole; N-2,3-dichlorophenyltetrachlorophthalamic acid; 5-methyl s-triazolo-(3,4-b)-benzthiazole; O,O-diisopropyl-S-benzylphosphorothioate; pentachloronitrobenzene; Kasugamycin; brasticidin S; 4,5,6,7-tetrachlorophthalide and the like, insecticides such as O,O-diethyl O-(2-isopropyl-4-methyl-6-pyrimidinyl)phosphorothioate; O,O-diethyl S-2-[(ethylthio)ethyl]phosphorodithioate; 1-naphthyl N-methylcarbamate; O,O-dimethyl O-(3-methyl-4-nitrophenyl)-thiophosphate; O,O-dimethyl S-(N-methylcarbamoylmethyl)phosphorodithioate; S-methyl-N-[(methylcarbamoyl)oxy]thioacetimidate; O,O-dimethyl S-(N-methyl-N-formylcarbamoylmethyl)phosphorodithioate, O,O-dimethyl S-2-(ethylthio)ethylphosphorodithioate; O,O-diethyl S-2[(ethylthio)ethyl]phosphorodithioate; O,O-dimethyl-1-hydroxy-2,2,2-trichloroethylphosphonate and the like or fertilizers and so on.

In another aspect of this invention, there is provided a new class of the pyrazole compounds having the above formula (II) which also show herbicidal activities as seen with respect to the compounds having the above formula (I).

As a result of our further studying upon the finding previously explained herein, we have also found that other particular new pyrazole compounds, which are out of the scope of the compounds (I) including two known ones and defined by the above formula (II), have also considerable herbicidal activities, though not so prominent as in the compounds (I).

In view of this finding, the processes for the preparation of the compounds (II), the application thereof as a herbicide etc. are the substantially same as in the case of the compounds (I), but there may be mentioned the following compounds for the purpose of illustration only, in addition to those listed hereinabove with regard to the compounds (I):

1,3-dimethyl-4-(2,4-dichlorobenzoyl)-5-mercaptopyrazole, m.p. 85°–86° C.

1,3-dimethyl-4-(4-benzoylbenzoyl)-5-hydroxypyrazole, m.p. 194°–195° C.

1,3-dimethyl-4-(2,4-dichlorobenzoyl)-5-acetylthiopyrazole. $n_D^{17.5}$ 1.5890

Moreover, the most preferable group of the compounds having the above formula (II) is the same as in the compounds (I).

In the preparation of the compounds having the above formula (II) wherein Y is sulfur atom, it is practically suitable to employ the above Process B by the use of an alkali metal hydrosulfide instead of the alkali metal hydroxide.

The organic acid esters and salts of the compounds (II) may be readily prepared from the corresponding free compounds according to the above Processes C, D and E.

The preparation of the compound having the above formula (I) or (II) and the herbicidal composition containing the compound having the above formula (I) will be more fully illustrated by way of the following examples.

EXAMPLE 1

1,3-Dimethyl-4-(4-nitrobenzoyl)-5-hydroxypyrazole

In 22 ml. of dry dioxane is dissolved 2.24 g. of 1,3-dimethyl-5-pyrazolone and then 2.96 g. of calcium hydroxide is added thereto. 3.71 g. of p-nitrobenzoyl chloride is added dropwise thereto while stirring at room temperature. After completion of the dropwise addition, the mixture is heated under reflux for 1 hour. After completion of the reaction, the reaction mixture is allowed to cool and then 40 ml. of a 2N hydrochloric acid solution is added thereto. Crystalline substances thus separated are recovered by filtration and washed with water to give 4.38 g. of crude crystals. This product is recrystallized from methanol to give 3.62 g. of the desired product as pale yellow columns having a melting point of 234°–235° C. Yield 69.3%

Analysis for $C_{12}H_{11}N_3O_4$(%): Calculated: C, 55.17; H, 4.24; N, 16.09; Found: C, 55.17; H, 4.14; N, 16.06

EXAMPLE 2

1,3-Dimethyl-4-(2,4-dichlorobenzoyl)-5-hydroxypyrazole

In 65 ml. of isopropanol are suspended 4.48 g. of 1,3-dimethyl-5-pyrazolone and 3 g. of calcium hydroxide and the resulting suspension is heated under reflux for 30 minutes with stirring. After cooling, 8.4 g. of 2,4-dichlorobenzoyl chloride is added dropwise thereto. After completion of the dropwise addition, the mixture is heated under reflux for 2 hours. The solvent is distilled off from the reaction mixture and 15 ml. of water is added to the residue. The mixture is made acidic with 23 ml. of a 2N hydrochloric acid solution and extracted with 60 ml. of chloroform. The chloroform layer is washed with water and the organic phase is separated and dried. The chloroform is distilled off. The residue is recrystallized from ethanol to give 7.6 g. of the desired product as colorless prisms of mp. 165°–166° C. Yield 66.7%

Analysis for $C_{12}H_{11}N_3O_4$(%): Calculated: C, 50.55; H, 3.53; N, 9.82; Cl, 24.88; Found: C, 50.85; H, 3.54; N, 9.81; Cl, 24.55.

EXAMPLE 3

1-Methyl-3-n-propyl-4-(2-chlorobenzoyl)-5-hydroxypyrazole 1.4 g. of 1-methyl-3-n-propyl-5-pyrazolone is dissolved in 10 ml. of dioxane with heating and then 1.5 g. of calcium hydroxide is added to the resulting solution. 1.75 g. of 2-chlorobenzoyl chloride is added dropwise with stirring at 50° C. After completion of the dropwise addition, the mixture is heated under reflux for 1 hour. After completion of the reaction, the reaction mixture is allowed to cool and 100 ml. of a 2N hydrochloric acid solution is added thereto. The mixture is extracted with 70 ml. of chloroform and an organic layer is separated. The layer is washed with water, dried over anhydrous sodium sulfate and the solvent is distilled off from the layer to give 2 g. of brown oily residue. The residue thus obtained is dissolved in a small amount of benzene and adsorbed on a silica gel column, which is then eluted with benzene: ethanol (50:1) to give 0.6 g. of crystals. The crystals are recrystallized from methanol-water (7:3) to give 0.25 g. of the desired product as colorless columns having a melting point of 125°–126° C. Yield 9.2%

Analysis for $C_{14}H_{15}ClN_2O_2$(%): Calculated: C, 60.33; H, 5.42; N, 10.05; Cl, 12.72; Found: C, 60.44; H, 5.43; N, 10.25; Cl, 12.72.

According to the procedures as in the above Examples 1 to 3, the following compounds are prepared.

1,3-dimethyl-4-(3-chlorobenzoyl)-5-hydroxypyrazole; m.p. 176.5°–177.5° C.
1,3-dimethyl-4-(4-chlorobenzoyl)-5-hydroxypyrazole; m.p. 202°–204° C.
1,3-dimethyl-4-(2-chlorobenzoyl)-5-hydroxypyrazole; m.p. 154°–155° C.
1,3-dimethyl-4-(3,4-dichlorobenzoyl)-5-hydroxypyrazole; m.p. 255°–257° C.
1,3-dimethyl-4-(4-methylbenzoyl)-5-hydroxypyrazole; m.p. 114°–116° C.
1,3-dimethyl-4-(3-methylbenzoyl)-5-hydroxypyrazole; m.p. 145°–146° C.
1,3-dimethyl-4-(2-methoxybenzoyl)-5-hydroxypyrazole; m.p. 162.5°–163.5° C.
1,3-dimethyl-4-(3-nitrobenzoyl)-5-hydroxypyrazole; m.p. 246°–247° C.
1,3-dimethyl-4-(3,5-dinitrobenzoyl)-5-hydroxypyrazole; m.p. 261°–262° C.
1,3-dimethyl-4-(4-bromobenzoyl)-5-hydroxypyrazole; m.p. 207°–208° C.
1,3-dimethyl-4-(3,5-dichlorobenzoyl)-5-hydroxypyrazole; m.p. 248°–249° C.
1,3-dimethyl-4-(2-nitrobenzoyl)-5-hydroxypyrazole; m.p. 233°–234° C.
1,3-dimethyl-4-(4-benzoylbenzoyl)-5-hydroxypyrazole; m.p. 194°–195° C.
1,3-dimethyl-4-(2-fluorobenzoyl)-5-hydroxypyrazole; m.p. 158°–159° C.
1,3-dimethyl-4-(2-bromobenzoyl)-5-hydroxypyrazole; m.p. 154°–156° C.
1,3-dimethyl-4-(2,5-dichlorobenzoyl)-5-hydroxypyrazole; m.p. 183°–184° C.
1,3-dimethyl-4-(4-methoxybenzoyl)-5-hydroxypyrazole; m.p. 214°–216° C.
1,3-dimethyl-4-(3,4-dimethoxybenzoyl)-5-hydroxypyrazole; m.p. 154°–155° C.
1,3-dimethyl-4-(4-tert.-butylbenzoyl)-5-hydroxypyrazole; m.p. 172°–173° C.
1,3-dimethyl-4-(3,4-dimethylbenzoyl)-5-hydroxypyrazole; m.p. 197°–198° C.
1,3-dimethyl-4-(3,5-dimethylbenzoyl)-5-hydroxypyrazole; m.p. 165°–167° C.
1,3-dimethyl-4-(2-chloro-4-nitrobenzoyl)-5-hydroxypyrazole; m.p. 197°–197.5° C.
1-methyl-4-(2-chlorobenzoyl)-5-hydroxypyrazole; m.p. 107°–110° C.
1,3-dimethyl-4-(3,5-dimethoxybenzoyl)-5-hydroxypyrazole; m.p. 181°–182° C.

1,3-dimethyl-4-(2-nitro-5-methylbenzoyl)-5-hydroxypyrazole; m.p. 257°–258° C.

1,3-dimethyl-4-(4-methanesulfonylbenzoyl)-5-hydroxypyrazole; m.p. 257°–259° C.

1-isopropyl-3-methyl-4-(2-chlorobenzoyl)-5-hydroxypyrazole; $n_D^{16}$ 1.5705

1,3-dimethyl-4-(2-iodobenzoyl)-5-hydroxypyrazole; m.p. 171°–172° C.

1,3-dimethyl-4-(4-fluorobenzoyl)-5-hydroxypyrazole; m.p. 181° C.

1,3-dimethyl-4-(4-cyanobenzoyl)-5-hydroxypyrazole; m.p. 208° C.

1,3-dimethyl-4-(2-acetylbenzoyl)-5-hydroxypyrazole; m.p. 142°–143° C.

1,3-dimethyl-4-(2,4,5-trichlorobenzoyl)-5-hydroxypyrazole; m.p. 156°–157° C.

1,3-dimethyl-4-(2,3,4,5-tetrachlorobenzoyl)-5-hydroxypyrazole; m.p. 225°–226° C.

1,3-dimethyl-4-(3-methyl-4-nitrobenzoyl)-5-hydroxypyrazole; m.p. 252°–254° C.

1,3-dimethyl-4-(2-nitro-4-chlorobenzoyl)-5-hydroxypyrazole; m.p. 223°–224° C.

1,3-dimethyl-4-(3,4,5-trimethoxybenzoyl)-5-hydroxypyrazole; m.p. 189°–191° C.

1-ethyl-3-methyl-4-(2,4-dichlorobenzoyl)-5-hydroxypyrazole; m.p. 176°–177° C.

1-ethyl-3-methyl-4-(2-nitro-4-chlorobenzoyl)-5-hydroxypyrazole; m.p. 196°–197° C.

EXAMPLE 4

1,3-Dimethyl-4-(2,4-dichlorobenzoyl)-5-mercaptopyrazole 1.0 g. of 5-chloro-1,3-dimethylpyrazole, 1.05 g. of anhydrous aluminum chloride and 1.66 g. of 2,4-dichlorobenzoyl chloride are dissolved in 6 ml. of tetrachloroethane and the resulting solution is heated under reflux for 8 hours. After completion of the reaction, the reaction mixture is poured into water and an organic layer is separated. 7 ml. of a 5% aqueous solution of sodium hydroxide is added thereto and the mixture is stirred for 1 hour. Then, the organic layer is dried over anhydrous sodium sulfate and the solvent is distilled off from the layer. The resulting oily substance is crystallized from ethanol to give 1.82 g. of 5-chloro-4-(2,4-dichlorobenzoyl)-1,3-dimethylpyrazole as prisms melting at 101.5°–102.5° C. Yield 78.3%

Analysis for $C_{12}H_9Cl_3N_2O$ (%): Calculated: C, 47.48; H, 2.99; N, 9.23; Cl, 35.04; Found: C, 47.49; H, 2.96; N, 9.31; Cl, 34.91.

A mixture of 0.3 g. of 5-chloro-4-(2,4-dichlorobenzoyl)-1,3-dimethylpyrazole, 2.1 g. of sodium hydrogen sulfide 2 hydrate and 6 ml. of ethanol is heated under reflux on a water bath for 3 hours. After completion of the reaction, the ethanol is distilled off under reduced pressure from the reaction mixture and 15 ml. of water is added followed by extraction with benzene. To an aqueous layer is added conc. hydrochloric acid to adjust the pH to 1 and the mixture is extracted with chloroform. The extract is washed with water and then dried over anhydrous sodium sulfate. The solvent is distilled off from the extract to give the crude crystalline substance, which is then recrystallized from n-hexane to give 0.10 g. of the desired product as yellow powders having a melting point of 85°–86° C. Yield 33.3%.

Analysis for $C_{12}H_{10}N_2OSCl_2$(%): Calculated: C, 47.85; H, 3.35; N, 9.30; S, 10.65; Cl, 23.54; Found: C, 47.76; H, 3.43; N, 9.38; S, 11.02; Cl, 23.24

EXAMPLE 5

1,3-Dimethyl-4-(2,6-dichlorobenzoyl)-5-hydroxypyrazole

In 5 ml. of water is dissolved 0.56 g. of potassium hydroxide and a solution of 1.52 g. of 5-chloro-4-(2,6-dichlorobenzoyl)-1,3-dimethylpyrazole in 10 ml. of ethanol is added thereto. The mixture is heated under reflux for 12 hours. After completion of the reaction, the reaction mixture is allowed to cool and extracted with benzene. An aqueous layer is separated and 2N HCl solution is added to adjust the pH to 3–4, whereby crystalline substance is separated out. The resulting crystalline substance is recovered by filtration and recrystallized from ethanol to give 0.68 g. of the desired product as colorless needles melting at 249.5°–250.5° C. Yield 48.0%.

Analysis for $C_{12}H_{10}Cl_2N_2O_2$ (%): Calculated: C, 50.55; H, 3.53; N, 9.82; Cl, 24.88; Found: C, 50.38; H, 3.53; N, 9.90; Cl, 24.57

In accordance with the procedures of the abovementioned Example 5 are prepared the following compounds.

1,3-dimethyl-4-(2,4-dimethylbenzoyl)-5-hydroxypyrazole; m.p. 95°–96° C.

1,3-dimethyl-4-(2-methylbenzoyl)-5-hydroxypyrazole; m.p. 82°–83° C.

EXAMPLE 6

1,3-Dimethyl-4-(2-chlorobenzoyl)-5-acetoxypyrazole

In a mixture of 20 ml. of benzene and 0.51 g. of triethylamine is dissolved 1.25 g. of 1,3-dimethyl-4-(2-chlorobenzoyl)-5-hydroxypyrazole and 0.4 g. of acetyl chloride is added dropwise at room temperature with stirring. After completion of the dripwise addition, the mixture is stirred at room temperature for 3 hours. After completion of the reaction, water is added to the reaction mixture to dissolve the salts and an organic layer is separated. The organic layer is dried over anhydrous sodium sulfate and the solvent is distilled off. The resulting oily substance is recrystallized from n-hexane to give crude crystalline substance. The substance is recrystallized from methanol to give 1.20 g. of the desired product as colorless prisms melting at 78°–79° C. Yield 82.2%.

Analysis for $C_{14}H_{13}ClN_2O_3$ (%): Calculated: C, 57.45; H, 4.48; N, 9.57; Cl, 12.11; Found: C, 57.50; H, 4.45; N, 9.61; Cl, 12.23

IR spectrum Nujol $\nu_{c=o}$: 1793 cm$^{-1}$

EXAMPLE 7

1,3-Dimethyl-4-(2,4-dichlorobenzoyl)-5-lauroyloxypyrazole

In 10 ml. of benzene is dissolved 0.285 g. of 1,3-dimethyl-4-(2,4-dichlorobenzoyl)-5-hydroxypyrazole and then 0.2 ml. of triethylamine is added thereto. Under ice-cooling, a solution of 0.27 g. of lauroyl chloride in 5 ml. of benzene is added dropwise thereto. After completion of the dropwise addition, the resulting mixture is stirred at room temperature for 19 hours. After completion of the reaction, ether is added to the reaction mixture, which is then washed successively with water, 1N HCl, a saturated aqueous solution of sodium hydrogencarbonate and a saturated aqueous solution of sodium chloride. Then, the reaction mixture is dried over anhydrous sodium sulfate and the solvent is distilled off from the reaction mixture. The resulting residue is recrystallized from n-hexane under cooling with dry-ice to give 0.46 g. of the desired product as white crystals melting at 56° C. Yield 98.0%.

Analysis for $C_{24}H_{32}Cl_2N_2O_3$ (%): Calculated: C, 61.66; H, 6.90; N, 5.99; Cl, 15.17; Found: C, 61.27; H, 6.94; N, 5.84; Cl, 15.11

IR spectrum Nujol $\nu_{C=O}$: 1790 cm$^{-1}$

EXAMPLE 8

1,3-Dimethyl-4-(2,4-dichlorobenzoyl)-5-chloroacetoxypyrazole

In a mixture of 10 ml. of benzene and 0.2 ml. of triethylamine is dissolved 0.285 g. of 1,3-dimethyl-4-(2,4-dichlorobenzoyl)-5-hydroxypyrazole and then a solution of 0.18 g. of chloroacetylchloride in 5 ml. of benzene is added dropwise under ice-cooling and stirring. After completion of the dropwise addition, the resulting mixture is stirred at room temperature for 2 hours. After completion of the reaction, ether is added to the reaction mixture and the mixture is then washed successively with 3 portions of 50 ml. of water and dried over anhydrous sodium sulfate. Then, the solvent is distilled off from the mixture and the resulting residue is recrystallized from n-hexane to give 0.297 g. of the desired product as white crystals melting at 120°–122° C. Yield 82.0%.

Analysis for $C_{14}H_{11}Cl_3N_2O_3$ (%): Calculated: C, 46.50; H, 3.07; N, 7.25; Cl, 29.41; Found: C, 46.25; H, 3.08; N, 7.81; Cl, 29.32

IR spectrum Nujol $\nu_{C=O}$: 1790 cm$^{-1}$

In accordance with the procedures of the abovementioned Examples 6–8 are prepared the following compounds.

1,3-dimethyl-4-(2-chlorobenzoyl)-5-(N,N-dimethylcarbamoyloxy)pyrazole; m.p. 115°–116° C.
1,3-dimethyl-4-(2,4-dichlorobenzoyl)-5-stearoyloxypyrazole; m.p. 57°–61° C.
1,3-dimethyl-4-(2,4-dichlorobenzoyl)-5-crotonyloxypyrazole; m.p. 87°–89° C.
1,3-dimethyl-4-(2,4-dichlorobenzoyl)-5-benzoyloxypyrazole; m.p. 138°–139° C.
1,3-dimethyl-4-(2,4-dichlorobenzoyl)-5-acetoxypyrazole; m.p. 81°–82° C.
1,3-dimethyl-4-(2,4-dichlorobenzoyl)-5-acetylthiopyrazole; $n_D^{17.5}$ 1.5890
1,3-dimethyl-4-(2,4-dichlorobenzoyl)-5-propionyloxypyrazole; m.p. 48° C.
1,3-dimethyl-4-(2,4-dichlorobenzoyl)-5-isobutyryloxypyrazole; m.p. 101°–102° C.
1,3-dimethyl-4-(2,4-dichlorobenzoyl)-5-linoleyloxypyrazole; $n_D^{13.8}$ 1.5196
1,3-dimethyl-4-(2-chloro-4-nitrobenzoyl)-5-benzoyloxypyrazole; m.p. 163° C.
1,3-dimethyl-4-(2-chloro-4-nitrobenzoyl)-5-(4-chlorobenzoyloxy)pyrazole; m.p. 194° C.
1,3-dimethyl-4-(2-chloro-4-nitrobenzoyl)-5-(2-chloro-4-nitrobenzoyloxy)pyrazole; m.p. 182°–184° C.
1,3-dimethyl-4-(2-chloro-4-nitrobenzoyl)-5-cinnamoyloxypyrazole; m.p. 164° C.
bis[1,3-dimethyl-4-(2-chloro-4-nitrobenzoyl)-5-pyrazolyl]succinate; m.p. 203° C.
1,3-dimethyl-4-(2-chloro-4-nitrobenzoyl)-5-acetoxypyrazole; m.p. 133° C.
1,3-dimethyl-4-(2-chloro-4-nitrobenzoyl)-5-pivaloyloxypyrazole; m.p. 157°–158° C.
1,3-dimethyl-4-(2,4-dichlorobenzoyl)-5-phenylacetoxypyrazole; m.p. 74°–76° C.
1,3-dimethyl-4-(2,4-dichlorobenzoyl)-5-(4-chlorophenylacetoxy)pyrazole; m.p. 130°–131° C.
1,3-dimethyl-4-(4-nitrobenzoyl)-5-acetoxypyrazole; m.p. 179°–180° C.
1,3-dimethyl-4-(2,4-dichlorobenzoyl)-5-cyclohexylcarbonylpyrazole; m.p. 98°–99° C.
1,3-dimethyl-4-(2,4-dichlorobenzoyl)-5-(2,4-dichlorophenoxyacetoxy)pyrazole; m.p. 107°–108° C.
1,3-dimethyl-4-(2,4-dichlorobenzoyl)-5-(2,4-dichlorobenzoyloxy)pyrazole; m.p. 168°–169° C.
bis[1,3-dimethyl-4-(2,4-dichlorobenzoyl)-5-pyrazolyl]sebacate; m.p. 143°–144° C.
1,3-dimethyl-4-(2,4-dichlorobenzoyl)-5-(4-methylbenzoyloxy)pyrazole; m.p. 197°–198° C.
1,3-dimethyl-4-(2,4-dichlorobenzoyl)-5-pivaloyloxypyrazole; m.p. 94° C.

EXAMPLE 9

1,3-Dimethyl-4-(2,4-dichlorobenzoyl)-5-pyrazolylmethanesulfonate

In a mixture of 0.1 g. of triethylamine and 5 ml. of dry benzene is dissolved 0.29 g. of 1,3-dimethyl-4-(2,4-dichlorobenzoyl)-5-hydroxypyrazole and then 0.1 g. of methanesulfonyl chloride is added dropwise at room temperature with stirring. After completion of the dropwise addition, the resulting mixture is stirred at room temperature for 12 hours. After completion of the reaction, 10 ml. of water is added to the reaction mixture. Then, an organic layer is separated. The organic layer is dried over anhydrous sodium sulfate and the solvent is distilled off. The resulting residue is recrystallized from n-hexane to give 0.3 g. of the desired product as white needles melting at 73°–74° C. Yield 83.3%.

Analysis for $C_{13}H_{12}Cl_2N_2O_4S$ (%): Calculated: C, 42.99; H. 3.33; N, 7.71; S, 8.83; Cl, 19.25; Found: C, 42.64; H, 3.37; N, 7.76;1 S, 9.15; Cl, 19.23

IR spectrum Nujol $\nu_{SO2}$: 1355 cm$^{-1}$; 1180 cm$^{-1}$

In accordance with the procedures of the above-mentioned Example 9 are prepared the following compounds.

1,3-dimethyl-4-(2,4-dichlorobenzoyl)-5-pyrazolyl 4-toluenesulfonate; m.p. 122°–124° C.
1,3-dimethyl-4-(2,4-dichlorobenzoyl)-5-pyrazolyl benzenesulfonate; m.p. 88°–89° C.
1,3-dimethyl-4-(2-nitro-4-chlorobenzoyl)-5-pyrazolyl 4-toluenesulfonate; m.p. 129°–130° C.
1,3-dimethyl-4-(2-nitro-4-chlorobenzoyl)-5-pyrazolyl benzenesulfonate; m.p. 127°–128° C.
1-ethyl-3-methyl-4-(2,4-dichlorobenzoyl)-5-pyrazolyl 4-toluenesulfonate; m.p. 115°–116° C.
1-ethyl-3-methyl-4-(2-nitro-4-chlorobenzoyl)-5-pyrazolyl 4-toluenesulfonate; m.p. 100°–101° C.
1,3-dimethyl-4-(2-chlorobenzoyl)-5-pyrazolyl methanesulfonate m.p. 97°–98° C.

EXAMPLE 10

1,3-Dimethyl-4-(2,4-dichlorobenzoyl)-5-(5-methyl-3-oxo-4-isoxazolin-2-ylcarbonyloxy)pyrazole In 4 ml. of dry benzene is dissolved 0.1 g. of 3-hydroxy-5-methylisoxazole and then 0.5 g. of liquid phosgene is added thereto. After stirring at room temperature for 1 hour, the mixture is heated under reflux for 1 hour. After completion of the reaction, the reaction mixture is allowed to cool and the excess phosgene and benzene are distilled off under reduced pressure. The residue is dissolved in 5 ml. of dry benzene and a solution of 0.3 g. of 4-(2,4-dichlorobenzoyl)-1,3-dimethyl-5-hydroxypyrazole and 0.1 g. of triethylamine in 5 ml. of dry benzene is added dropwise at room temperature with stirring. After completion of the dropwise addition, the mixture is stirred at room temperature for further 1 hour. After completion of the reaction, 10 ml. of water is added to the reaction mixture and then an organic layer is separated. The organic layer is washed successively with 1N HCl, a saturated aqueous solution of sodium hydrogen carbonate and water and dried over anhydrous sodium sulfate. Then, the solvent is distilled off and the resulting residue is recrystallized from benzene-hexane to give 0.25 g. of the desired product as white needles melting at 180°–182° C. Yield 61.0%.

Analysis for $C_{17}H_{13}Cl_2N_3O_5$(%): Calculated: C, 49.78; H, 3.19; N, 10.24; Cl, 17.28; Found: C, 49.75; H, 3.31; N, 10.31; Cl, 17.05

IR spectrum Nujol $\nu_{c=o}$: 1785 cm$^{-1}$

In accordance with the procedures of the above-mentioned Example 10 is prepared the following compound.

1,3-dimethyl-4-(2,4-dichlorobenzoyl)-5-(3-oxo-4-chloro-5-methyl-4-isoxazolin-2-ylcarbonyloxy)-pyrazole; m.p. 204°–206° C.

EXAMPLE 11

1,3-Dimethyl-4-(2,4-dichlorobenzoyl)-5-methoxycarbonyloxypyrazole

In a mixture of 20 ml. of dry benzene and 0.28 g. of triethylamine is dissolved 0.72 g. of 1,3-dimethyl-4-(2,4-dichlorobenzoyl)-5-hydroxypyrazole and then 0.26 g. of methyl chlorocarbonate is added dropwise at room temperature with stirring. After completion of the dropwise addition, the mixture is stirred at room temperature for 1 hour. After completion of the reaction, the reaction mixture is allowed to stand for 12 hours and then 30 ml. of water is added thereto. Then, a benzene layer is separated and an aqueous layer is extracted with benzene. The benzene layer and the benzene extract are combined and the mixture is washed with water and dried over anhydrous sodium sulfate. Then, the solvent is distilled off from the benzene solution and the resulting residue is recrystallized from a small amount of n-hexane to give 0.77 g. of the desired product as white crystals melting at 86°–88° C. Yield 92%.

Analysis for $C_{14}H_{12}Cl_2N_2O_4$(%): Calculated: C, 49.00; H, 3.52; N, 8.16; Cl, 20.66; Found: C, 49.05; H, 3.56; N, 8.33; Cl, 20.44

IR spectrum Nujol $\nu_{c=o}$: 1771 cm$^{-1}$

In accordance with the procedures of the above-mentioned Example 11 are prepared the following compounds.

1,3-dimethyl-4-(2-chlorobenzoyl)-5-methoxycarbonyloxypyrazole; m.p. 69°–70° C.
1,3-dimethyl-4-(2,4-dichlorobenzoyl)-5-n-propoxycarbonyloxypyrazole; m.p. 59°–62° C.
1,3-dimethyl-4-(2,4-dichlorobenzoyl)-5-benzyloxycarbonyloxypyrazole; m.p. 87°–90° C.
bis[1,3-dimethyl-4-(2,4-dichlorobenzoyl)-5-pyrazolyl]carbonate; m.p. 166°–168° C.
1,3-dimethyl-4-(2,4-dichlorobenzoyl)-5-phenoxycarbonyloxypyrazole; m.p. 159°–160° C.
1,3-dimethyl-4-(2,4-dichlorobenzoyl)-5-phenylthiocarbonyloxypyrazole; m.p. 83°–84° C.
1,3-dimethyl-4-(2,4-dichlorobenzoyl)-5-n-butylthiocarbonyloxypyrazole; $n_D^{16}$ 1.5618
1,3-dimethyl-4-(2,4-dichlorobenzoyl)-5-ethylthiocarbonyloxypyrazole; $n_D^{23}$ 1.5751
1,3-dimethyl-4-(2,4-dichlorobenzoyl)-5-benzylthiocarbonyloxypyrazole; $n_D^{23}$ 1.5904

EXAMPLE 12

O,O-Diethyl O-[1,3-dimethyl-4-(2-chlorobenzoyl)-5-pyrazolyl]phosphorothioate

A mixture of 1.0 g. of 4-(2-chlorobenzoyl)-1,3-dimethyl-5-hydroxypyrazole, 20 ml. of benzene, 0.433 g. of triethylamine and 0.81 g. of O,O-diethylthiophosphoric chloride is heated under reflux with stirring for 6.5 hours. After completion of the reaction, the reaction mixture is allowed to cool and water is added to dissolve salts. An organic layer is separated, washed with water, dried over anhydrous sodium sulfate and the solvent is distilled off. The resulting oily substance is columnchromatographed over 10 g. of silica gel and then recrystallized from n-hexane to give 0.28 g. of the desired product melting at 71°–74° C. Yield 17.8%.

Analysis for $C_{16}H_{20}Cl\ N_2O_4PS$ (%): Calculated: C, 47.41; H, 5.00; N, 6.95; Cl, 8.80; P, 7.69; Found: C, 47.83; H, 4.94; N, 6.76; Cl, 9.08; P, 7.35

EXAMPLE 13

1,3-Dimethyl-4-(2,4-dichlorobenzoyl)-5-hydroxypyrazole calcium salt

In 50 ml. of water is suspended 2.85 g. of 1,3-dimethyl-4-(2,4-dichlorobenzoyl)-5-hydroxypyrazole and the suspension is dissolved in about 5 ml. of a 2N aqueous solution of sodium hydroxide. A solution of 1.11 g. of calcium chloride in 10 ml. of water is added and the resulting mixture is stirred. The so separated precipitates are recovered by filtration and dried to give 2.4 g. of the desired product as white powder melting at about 260° C. Yield 79.0%.

Analysis for $C_{12}H_9N_2O_2Cl_2Ca/2.H_2O$ (%): Calculated: C, 44.73; H, 3.44; N, 8.69; Found: C, 47.88; H, 3.23; N, 8.83

In accordance with the procedure of the above-mentioned Example 13 are prepared the following compounds.

1,3-dimethyl-4-(2,4-dichlorobenzoyl)-5-hydroxypyrazole magnesium salt; m.p. ca. 270° C.
1,3-dimethyl-4-(2,4-dichlorobenzoyl)-5-hydroxypyrazole aluminum salt; m.p. ca. 155° C.
1,3-dimethyl-4-(2,4-dichlorobenzoyl)-5-hydroxypyrazole iron salt; m.p. ca. 170° C.
1,3-dimethyl-4-(2.4-dichlorobenzoyl)-5-hydroxypyraziole copper salt; m.p. above 300° C.
1,3-dimethyl-4-(2,4-dichlorobenzoyl)-5-hydroxypyrazole sodium salt; m.p. above 300° C.

EXAMPLE 14

1,3-Dimethyl-4-(2,4-dichlorobenzoyl)-5-hydroxypyrazole isopropylamine salt

In 50 ml. of benzene is suspended 2.85 g. of 1,3-dimethyl-4-(2,4-dichlorobenzoyl)-5-hydroxypyrazole and 0.7 g. of isopropylamine is added to the suspension with stirring. Then, the resulting mixture is stirred at room temperature for about 1 hour. The solvent is distilled off from the reaction mixture. The residue is cooled. The so separated solid material is recovered by filtration, washed with petroleum ether and dried to give 3.2 g. of the desired product as white powdery substance melting at 130°–140° C. Yield 93.2%.

Analysis for $C_{15}H_{19}Cl_2N_3O_2$ (%): Calculated: C, 52.34; H, 5.56; N, 12.21; Found: C, 52.09; H, 5.72; N, 12.59

EXAMPLE 15

1,3-Dimethyl-4-(2,4-dichlorobenzoyl)-5-hydroxypyrazole hydrochloride

To 0.3 g. of 1,3-dimethyl-4-(2,4-dichlorobenzoyl)-5-hydroxypyrazole is added 2 ml. of conc. HCl and the resulting mixture is stirred at room temperature for 6 hours. After completion of the reaction, the reaction mixture is allowed to cool and the so separated desired product is recovered by filtration. The product is washed with a small amount of methanol and then with n-hexane and next dried to give 0.20 g. of the desired product as white powders having a melting point of 115°–125° C. (with decomp.) Yield 57.1%.

Analysis for $C_{12}H_{11}N_2Cl_3O_2$ (%): Calculated: C, 44.82; H, 3.45; N, 8.71; Cl, 33.07; Found: C, 45.16; H, 3.57; N, 8.85; Cl, 32.93

In accordance with the procedures of the above-mentioned Example 15 is prepared the following compound.

1,3-dimethyl-4-(3,4-dimethoxybenzoyl)-5-hydroxypyrazole hydrochloride; m.p. 164°–165° C.

EXAMPLE 16

1-Allyl-3-methyl-4-(2,4-dichlorobenzoyl)-5-hydroxypyrazole

A suspension of 1.4 g. of 1-allyl-3-methyl-2-pyrazolin-5-one and 0.74 g. of calcium hydroxide in 20 ml. of isopropanol is heated under reflux with stirring for 1.5 hours. After cooling, to the resulting mixture is added dropwise 2.3 g. of 2,4-dichlorobenzoyl chloride. After completion of the dropwise addition, the resulting mixture is heated under reflux for 5.5 hours. After completion of the reaction, the solvent is distilled off from the reaction mixture and to the residue is added 3 ml. of 2N hydrochloric acid to adjust pH to 3.0. Then, the mixture is extracted with chloroform and the extract solvent is distilled off from the extract. The residue is dissolved in a small amount of benzene and the solution is washed with water, dried over anhydrous sodium sulfate and the solvent is distilled off. The resulting residue is recrystallized from isopropyl ether containing a small amount of methylene chloride to give 1.18 g. of the desired product as white crystals melting at 161°–163° C. Yield 40.7%.

Analysis for $C_{12}H_{16}N_2Cl_2O_3$ (%): Calculated: C, 47.86; H, 3.35; N, 9.30; Cl, 23.54; Found: C, 47.33; H, 3.41; N, 9.06; Cl, 23.31

EXAMPLE 17

1-Allyl-3-methyl-4-(2,4-dichlorobenzoyl)-5-pyrazolyl 4-toluenesulfonate

To a solution of 180 mg. of 1-allyl-3-methyl-4-(2,4-dichlorobenzoyl)-5-hydroxypyrazole in 6 ml. of benzene and 58.4 mg. of triethylamine is added dropwise 110 mg. of 4-toluenesulfonyl chloride with stirring at room temperature. Then, the resulting mixture is heated under reflux for 1 hour. After completion of the reaction, water is added to the reaction mixture and an organic layer is separated. The organic layer is dried over anhydrous sodium sulfate, the solvent is distilled off and the resulting oily substance is recrystallized from benzene-n-hexane to give 173 mg. of the desired product as colorless prisms melting at 113°–114° C. Further, the solvent is distilled off from the mother liquor and recrystallization from n-hexane gives 26 mg. of the desired product. Total yield 73.9%

Analysis for $C_{21}H_{18}O_4N_2S\ Cl_2$ (%): Calculated: C, 54.20; H, 3.90; N, 6.02; S, 6.89; Cl, 15.24; Found: C, 54.45; H, 3.98; N, 6.07; S, 6.80; Cl, 15.19

According to the same procedures as in Example 17 are prepared the following compounds:

1-allyl-3-methyl-4-(2,4-dichlorobenzoyl)-5-(4-chlorobenzoyloxy)pyrazole; m.p. 155°–157° C.

1-allyl-3-methyl-4-(2,4-dichlorobenzoyl)-5-isobutyryloxypyrazole; m.p. 62°–63° C.

1-allyl-3-methyl-4-(2-chloro-4-nitrobenzoyl)-5-pyrazolyl 4-toluenesulfonate; m.p. 96°–99° C.

Examples of the preparations of the present herbicidal composition are given below. All parts are given by weight hereinafter unless otherwise stated.

EXAMPLE 18

Granules 70 parts of the compound designated as Compound No. 11 are finely pulverized and 30 parts of clay are added thereto. The mixture is blended in a mixer to form a premix. 10 parts of the premix are homogeneously blended with 60 parts of clay and 30 parts of bentonite in a mixer. To the resulting blend is added an appropriate amount of water. The mixture is kneaded in a kneader, extruded through a screen having a diameter of 0.8 mm. and dried in a draft drier at 50° C. The so obtained product is adjusted by a shifter to give granules.

EXAMPLE 19

Granules 70 parts of the compound designated as Compound No. 183 are finely pulverized and 30 parts of clay are added thereto. The mixture is blended in a mixer to form a premix. 10 parts of the premix are homogeneously blended with 60 parts of clay and 30 parts of bentonite in a mixer. To the resulting blend is added an appropriate amount of water. The mixture is kneaded in a kneader, extruded through a screen having a diameter of 0.8 mm. and dried in a draft drier at 50° C. The so obtained product is adjusted by a shifter to give granules.

EXAMPLE 20

Granules 35 parts of the compound designated as Compound No. 11 and 35 parts of S-(4-chlorobenzyl)N,N-diethylthiolcarbamate are finly pulverized and 30 parts of white carbon are added thereto. The mixture is blended in a mixer to form a premix. 20 parts of the premix are homogeneously blended with 50 parts of clay and 30 parts of bentonite in a mixer. To the resulting blend is added an appropriate amount of water. The mixture is kneaded in a kneader, extruded through a screen having a diameter of 0.8 mm. and dried in a draft drier at 50° C. The so obtained product is adjusted by a shifter to give granules.

EXAMPLE 21

Wettable powders 50 parts of the compound designated as Compound No. 32, 29 parts of clay, 10 parts of diatomaceous earth, 5 parts of white carbon, 3 parts of sodium ligninsulfonate, 2 parts of "Newcoal" 1106 (trade name, Nihon Nyukazai K. K., Japan) and 1 part of polyvinyl alcohol are homogeneously blended in a mixer and pulverized three times by means of a hammer mill to give wettable powders.

EXAMPLE 22

Emulsifiable concentrates 20 parts of the compound designated as Compound No. 18, 65 parts of xylene and 15 parts of "Paracoal" PS (trade name, Nihon Nyukazai K. K., Japan) are blended and homogeneously dissolved to form emulsifiable concentrates.

EXAMPLE 23

Solutions 30 parts of the compound designated as Compound No. 69, 1 part of "Newcoal" 565 (trade name, Nihon Nyukazai K. K., Japan) and 69 parts of water are blended and homogeneously dissolved to form solutions.

Experimental examples of the present herbicidal compositions thus prepared are given below. The wettable powders prepared according to the procedures in the abovementioned Example 21 are used in the following experiments, each containing 50% by weight of the active compound of this invention.

EXPERIMENT 1

Water surface application tests for paddy field weed control 3 polyethylene pots (hereinafter abbreviated as A, B and C), each having the surface of 45 $cm^2$, were packed with paddy field soil. In Pot A were transplanted rice seedlings (two plants) (variety: Kinmaze at 2.5 leaf stage) and two tubers of "Urikawa" as a representative of perennial weed. In Pot B, seeds of monochoria, false pimpernel and "Abunome" (*Dopatrium junceum* Hamilt) as representative of broad-leaf weed were incorporated in the soil, a block of runners of slender spikerush was transplanted thereinto and two tubers of "Mizugayatsuri" as perenial weed were planted in the soil. In Pot C, seeds of barnyardgrass and "Hotarui" (*Scirpus hotarui* Ohwi) as representatives of narrow-leaf weed were incorporated in the soil and two tubers of "Omodaka" a perennial weed were planted in the soil. The Pots A, B and C were kept in a green house for 3 days under a paddy field condition. After rooting of plants, suspensions of test chemicals were applied into the paddy water at 10 ml. per Pot. After 20 days from the treatment, herbicidal effects on each weed and phytotoxicity to rice plant were observed and evaluated. The results are shown in Table 1 wherein effective does (g/a) means the minimum dose for growth inhibition rate to each test plant (percentage leaf area suffered chlorosis) of not less than 70%.

TABLE 1

| | Herbicidal Activity in Paddy Field (Effective dose g/a) | | | | | | | |
|---|---|---|---|---|---|---|---|---|
| Compound No. | Barnyard-grass | Broad-weed leaf | "Hotarui" | "Urikawa" | Slender spikerush | "Mizugaya-tsuri" | "Omodaka" | Rice seedling transplanted |
| 1 | 100 | 25 | 75 | 100 | 75 | 100 | 50 | >800 |
| 2 | 50 | 25 | 75 | 100 | 25 | 50 | 25 | >800 |
| 3 | 25 | 6.25 | 12.5 | 50 | 12.5 | 12.5 | 25 | 400 |
| 4 | 75 | 25 | 50 | 75 | 200 | 50 | 50 | 400 |
| 5 | 75 | 50 | 75 | 200 | 100 | 75 | 50 | >800 |
| 6 | 75 | 50 | 50 | 75 | 25 | 75 | 50 | 400 |
| 8 | 75 | 50 | 50 | 50 | 50 | 25 | 25 | 400 |
| 9 | 25 | 12.5 | 12.5 | 100 | 6.25 | 6.25 | 100 | 200 |
| 10 | 75 | 75 | 75 | 200 | 25 | 50 | 200 | >800 |
| 11 | 6.25 | 6.25 | 12.5 | 6.25 | 50 | 12.5 | 12.5 | 200 |
| 13 | 25 | 75 | 75 | 50 | 100 | 75 | 100 | 200 |
| 14 | 6.25 | 6.25 | 6.25 | 6.25 | 25 | 6.25 | 12.5 | 100 |
| 15 | 400 | 6.25 | 100 | 75 | 75 | 75 | 100 | >800 |
| 16 | 12.5 | 6.25 | 12.5 | 12.5 | 25 | 6.25 | 25 | 400 |
| 18 | 12.5 | 6.25 | 25 | 12.5 | 12.5 | 12.5 | 50 | 400 |
| 19 | 12.5 | 6.25 | 6.25 | 12.5 | 12.5 | 12.5 | 12.5 | 100 |
| 21 | 25 | 25 | 25 | 12.5 | 25 | 25 | 50 | 400 |
| 22 | 12.5 | 12.5 | 6.25 | 12.5 | 12.5 | 12.5 | 12.5 | 400 |
| 23 | 50 | 12.5 | 25 | 6.25 | 12.5 | 12.5 | 12.5 | >800 |
| 24 | 50 | 50 | 50 | 50 | 75 | 75 | 50 | 400 |
| 26 | 12.5 | 12.5 | 6.25 | 12.5 | 12.5 | 25 | 12.5 | 100 |
| 28 | 200 | 50 | 100 | 25 | 75 | 400 | 75 | 400 |
| 29 | 50 | 6.25 | 50 | 12.5 | 75 | 25 | 50 | 400 |
| 30 | 50 | 100 | 75 | 50 | 400 | 75 | 200 | >800 |
| 32 | 6.25 | 6.25 | 6.25 | 12.5 | 12.5 | 25 | 50 | 200 |
| 33 | 12.5 | 12.5 | 12.5 | 75 | 100 | 25 | 75 | 400 |
| 35 | 25 | 12.5 | 25 | 12.5 | 50 | 25 | 25 | >800 |
| 36 | 12.5 | 6.25 | 25 | 25 | 75 | 200 | 50 | >800 |
| 38 | 25 | 6.25 | 12.5 | 12.5 | 12.5 | 12.5 | 12.5 | 200 |
| 39 | 6.25 | 6.25 | 6.25 | 6.25 | 50 | 25 | 25 | 100 |
| 40 | 50 | 50 | 75 | 6.25 | 75 | 75 | 50 | >800 |
| 41 | 6.25 | 12.5 | 6.25 | 12.5 | 25 | 12.5 | 25 | 400 |
| 42 | 25 | 12.5 | 50 | 100 | 100 | 400 | 100 | >800 |
| 43 | 6.25 | 25 | 50 | 50 | 100 | 75 | 100 | 200 |
| 44 | 6.25 | 12.5 | 12.5 | 25 | 25 | 25 | 25 | 400 |
| 45 | 25 | 6.25 | 12.5 | 12.5 | 12.5 | 12.5 | 12.5 | 200 |

TABLE 1-continued

Herbicidal Activity in Paddy Field
(Effective dose g/a)

| Compound No. | Barnyard-grass | Broad-weed leaf | "Hotarui" | "Urikawa" | Slender spikerush | "Mizugaya-tsuri" | "Omodaka" | Rice seedling trans-planted |
|---|---|---|---|---|---|---|---|---|
| 46 | 25 | 6.25 | 12.5 | 12.5 | 12.5 | 12.5 | 12.5 | 400 |
| 47 | 6.25 | 6.25 | 6.25 | 6.25 | 12.5 | 6.25 | 12.5 | >800 |
| 48 | 6.25 | 6.25 | 6.25 | 12.5 | 6.25 | 6.25 | 12.5 | 200 |
| 49 | 6.25 | 6.25 | 6.25 | 12.5 | 25 | 12.5 | 12.5 | 200 |
| 51 | 12.5 | 6.25 | 12.5 | 12.5 | 12.5 | 6.25 | 50 | 400 |
| 52 | 50 | 6.25 | 50 | 75 | 75 | 25 | 75 | >800 |
| 53 | 100 | 6.25 | 50 | 6.25 | 50 | 50 | 50 | >800 |
| 54 | 200 | 6.25 | 200 | 12.5 | 75 | 75 | 100 | >800 |
| 56 | 6.25 | 6.25 | 6.25 | 12.5 | 12.5 | 12.5 | 6.25 | 400 |
| 57 | 6.25 | 6.25 | 12.5 | 6.25 | 6.25 | 6.25 | 12.5 | 200 |
| 58 | 6.25 | 6.25 | 6.25 | 12.5 | 12.5 | 12.5 | 12.5 | 200 |
| 59 | 6.25 | 6.25 | 25 | 12.5 | 6.25 | 6.25 | 12.5 | 400 |
| 60 | 6.25 | 6.25 | 12.5 | 25 | 12.5 | 12.5 | 12.5 | 400 |
| 61 | 6.25 | 6.25 | 12.5 | 6.25 | 25 | 6.25 | 12.5 | 200 |
| 63 | 6.25 | 6.25 | 12.5 | 12.5 | 6.25 | 12.5 | 6.25 | 100 |
| 64 | 12.5 | 6.25 | 12.5 | 6.25 | 6.25 | 6.25 | 25 | 200 |
| 65 | 12.5 | 6.25 | 12.5 | 12.5 | 12.5 | 6.25 | 12.5 | 200 |
| 66 | 12.5 | 6.25 | 6.25 | 12.5 | 6.25 | 12.5 | 25 | 200 |
| 67 | 6.25 | 6.25 | 6.25 | 12.5 | 6.25 | 6.25 | 12.5 | 200 |
| 68 | 12.5 | 6.25 | 12.5 | 12.5 | 25 | 6.25 | 12.5 | 200 |
| 69 | 6.25 | 6.25 | 12.5 | 12.5 | 12.5 | 6.25 | 12.5 | 200 |
| 71 | 12.5 | 6.25 | 12.5 | 25 | 25 | 25 | 75 | 100 |
| 72 | 12.5 | 12.5 | 25 | 25 | 100 | 12.5 | 25 | 400 |
| 73 | 12.5 | 6.25 | 12.5 | 12.5 | 50 | 12.5 | 25 | 400 |
| 74 | 12.5 | 6.25 | 12.5 | 25 | 25 | 12.5 | 25 | 200 |
| 76 | 6.25 | 6.25 | 12.5 | 6.25 | 25 | 6.25 | 25 | 400 |
| 77 | 6.25 | 6.25 | 6.25 | 6.25 | 12.5 | 12.5 | 12.5 | 200 |
| 78 | 12.5 | 6.25 | 25 | 25 | 50 | 50 | 50 | 400 |
| 79 | 6.25 | 6.25 | 12.5 | 12.5 | 25 | 12.5 | 100 | 400 |
| 80 | 6.25 | 6.25 | 6.25 | 12.5 | 25 | 6.25 | 25 | 400 |
| 81 | 6.25 | 6.25 | 25 | 6.25 | 50 | 6.25 | 25 | 200 |
| 82 | 6.25 | 6.25 | 6.25 | 12.5 | 25 | 200 | 12.5 | 200 |
| 83 | 6.25 | 6.25 | 6.25 | 12.5 | 50 | 6.25 | 12.5 | 200 |
| 84 | 12.5 | 12.5 | 25 | 12.5 | 25 | 25 | 12.5 | 200 |
| 85 | 6.25 | 6.25 | 12.5 | 12.5 | 25 | 6.25 | 25 | 200 |
| 86 | 12.5 | 12.5 | 25 | 6.25 | 25 | 6.25 | 25 | 400 |
| 87 | 12.5 | 12.5 | 6.25 | 12.5 | 12.5 | 6.25 | 50 | >800 |
| 88 | 25 | 12.5 | 25 | 25 | 25 | 25 | 25 | 400 |
| 90 | 25 | 12.5 | 25 | 12.5 | 25 | 12.5 | 12.5 | 400 |
| 91 | 12.5 | 6.25 | 12.5 | 12.5 | 25 | 12.5 | 12.5 | 400 |
| 92 | 200 | 6.25 | 75 | 50 | 75 | 75 | 100 | >800 |
| 94 | 25 | 12.5 | 12.5 | 75 | 12.5 | 25 | 75 | 200 |
| 95 | 6.25 | 6.25 | 12.5 | 12.5 | 25 | 6.25 | 25 | 200 |
| 96 | 6.25 | 6.25 | 6.25 | 6.25 | 6.25 | 12.5 | 6.25 | 100 |
| 97 | 12.5 | 6.25 | 25 | 12.5 | 25 | 12.5 | 12.5 | 200 |
| 98 | 75 | 75 | 75 | 25 | 25 | 50 | 200 | >800 |
| 100 | 12.5 | 12.5 | 25 | 25 | 25 | 25 | 25 | 400 |
| 101 | 12.5 | 25 | 6.25 | 12.5 | 50 | 25 | 25 | 200 |
| 102 | 25 | 12.5 | 12.5 | 6.25 | 50 | 25 | 50 | 400 |
| 103 | 12.5 | 6.25 | 12.5 | 6.25 | 25 | 50 | 50 | 400 |
| 104 | 12.5 | 12.5 | 25 | 6.25 | 25 | 25 | 12.5 | 400 |
| 105 | 6.25 | 12.5 | 25 | 25 | 25 | 12.5 | 25 | 100 |
| 106 | 12.5 | 12.5 | 25 | 25 | 25 | 12.5 | 25 | 100 |
| 107 | 25 | 50 | 25 | 6.25 | 50 | 50 | 50 | 400 |
| 108 | 25 | 25 | 25 | 12.5 | 50 | 25 | 50 | 100 |
| 109 | 25 | 50 | 50 | 12.5 | 50 | 50 | 50 | 400 |
| 110 | 25 | 12.5 | 75 | 50 | 25 | 50 | 25 | 400 |
| 111 | 12.5 | 25 | 25 | 12.5 | 50 | 50 | 25 | 400 |
| 112 | 25 | 25 | 50 | 12.5 | 50 | 50 | 25 | 400 |
| 115 | 12.5 | 12.5 | 25 | 12.5 | 50 | 25 | 12.5 | 400 |
| 125 | 6.25 | 12.5 | 12.5 | 25 | 25 | 12.5 | 50 | 200 |
| 135 | 12.5 | 25 | 50 | 12.5 | 50 | 25 | 25 | 400 |
| 141 | 12.5 | 12.5 | 25 | 6.25 | 25 | 25 | 12.5 | 400 |
| 183 | 25 | 12.5 | 25 | 6.25 | 12.5 | 50 | 25 | 400 |

EXPERIMENT 2

Pre-emergency application tests for upland weed control

In a polyethylene pot having the surface of 150 cm$^2$ were filled soil and seeds of barnyard grass, crabgrass, green foxtail, goose grass and "Kayatsurigusa" as representatives of narrow-leaf weed and of shepherd's purse as a representative of broad-leaf weed were sown and covered with soil.

Another polyethylene pot having the surface of 150 cm$^2$ was filled with soil and seeds of asatic dayflower as narrow-leaf weed and common chickweed, corn spurrey, pigweed, common pursland and common lamb's-quaters as representatives of broad-leaf weed were sown and covered with soil.

Immediately after soil-covering, suspensions of test compounds were applied to soil surface at the rate of 10 ml. per pot. After 20 days from the application, herbicidal effects on each weed were observed. The results are shown in Table 2 wherein ratings for evaluation are the same as in Experiment 1 and shown by means of effective dose (g/a).

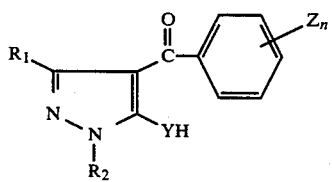

TABLE 2

| | Herbicidal activity in field (Effective dose g/a) | | | | | | | | | | |
|---|---|---|---|---|---|---|---|---|---|---|---|
| Compound No. | barnyard grass | crab-grass | green foxtail | goose grass | "Kayat-surigusa" | common chickweed | asatic dayflower | corn spurrey | pig-weed | common purslane | common lamb's-quarters | shepherd's purse |
| 3 | 50 | 50 | 50 | 50 | 25 | 25 | 400 | 25 | 200 | 100 | 50 | 50 |
| 4 | 100 | 100 | 50 | 50 | 25 | 200 | 400 | 400 | 50 | 50 | 100 | 100 |
| 9 | 50 | 25 | 50 | 25 | 25 | 100 | 100 | 400 | 50 | 200 | 100 | 100 |
| 11 | 50 | 200 | 400 | 400 | 50 | 25 | 400 | 25 | 200 | 50 | 50 | 50 |
| 14 | 25 | 50 | 25 | 25 | 25 | 25 | 100 | 25 | 50 | 50 | 25 | 25 |
| 16 | 200 | 200 | 200 | 200 | 25 | 100 | 800 | 100 | 800 | 25 | 25 | 400 |
| 19 | 50 | 25 | 25 | 25 | 25 | 25 | 100 | 25 | 50 | 25 | 25 | 25 |
| 26 | 100 | 100 | 100 | 25 | 25 | 200 | 400 | 400 | 50 | 25 | 50 | 50 |
| 32 | 25 | 25 | 50 | 25 | 25 | 400 | 100 | 25 | 25 | 25 | 25 | 25 |
| 38 | 100 | 200 | 400 | 50 | 25 | 25 | 100 | 25 | 800 | 25 | 100 | 50 |
| 39 | 25 | 25 | 50 | 25 | 25 | 25 | 100 | 25 | 25 | 25 | 100 | 25 |
| 43 | 25 | 25 | 25 | 25 | 25 | 25 | 100 | 25 | 50 | 25 | 25 | 25 |
| 44 | 100 | 50 | 50 | 50 | 25 | 25 | 200 | 50 | 100 | 25 | 25 | 50 |
| 47 | 50 | 50 | 25 | 50 | 25 | 25 | 50 | 25 | 50 | 25 | 25 | 25 |
| 49 | 50 | 100 | 100 | 50 | 25 | 25 | 200 | 25 | 100 | 25 | 25 | 25 |
| 51 | 200 | 200 | 200 | 100 | 25 | 25 | 200 | 25 | 100 | 25 | 25 | 25 |
| 56 | 100 | 400 | 100 | 100 | 25 | 25 | 200 | 25 | 25 | 25 | 25 | 25 |
| 57 | 100 | 400 | 100 | 100 | 25 | 25 | 200 | 25 | 25 | 25 | 25 | 25 |
| 58 | 100 | 200 | 100 | 200 | 25 | 25 | 50 | 25 | 25 | 25 | 50 | 25 |
| 59 | 100 | 400 | 100 | 200 | 25 | 25 | 400 | 25 | 50 | 25 | 25 | 25 |
| 60 | 100 | 400 | 100 | 100 | 25 | 25 | 200 | 25 | 100 | 200 | 25 | 25 |
| 61 | 100 | 800 | 100 | 100 | 25 | 25 | 200 | 25 | 25 | 50 | 25 | 25 |
| 63 | 100 | 200 | 100 | 100 | 25 | 25 | 100 | 25 | 25 | 25 | 25 | 25 |
| 64 | 100 | 400 | 100 | 100 | 25 | 25 | 200 | 25 | 200 | 25 | 25 | 25 |
| 65 | 100 | 800 | 200 | 400 | 25 | 25 | 25 | 200 | 50 | 25 | 25 | 25 |
| 66 | 100 | 800 | 100 | 400 | 25 | 25 | 25 | 100 | 50 | 25 | 25 | 25 |
| 67 | 200 | 800 | 50 | 100 | 25 | 25 | 25 | 25 | 25 | 25 | 25 | 25 |
| 68 | 100 | 200 | 100 | 100 | 25 | 25 | 200 | 50 | 25 | 25 | 25 | 25 |
| 69 | 100 | 400 | 100 | 100 | 25 | 25 | 200 | 25 | 50 | 25 | 25 | 25 |
| 76 | 100 | 100 | 100 | 50 | 25 | 25 | 200 | 25 | 25 | 50 | 25 | 25 |
| 78 | 100 | 100 | 200 | 200 | 25 | 100 | 800 | 200 | 400 | 200 | 100 | 200 |
| 79 | 100 | 100 | 100 | 100 | 25 | 200 | 800 | 200 | 100 | 100 | 100 | 100 |
| 80 | 25 | 50 | 50 | 50 | 25 | 25 | 200 | 50 | 25 | 25 | 50 | 25 |
| 81 | 50 | 50 | 25 | 25 | 25 | 25 | 100 | 25 | 25 | 25 | 25 | 25 |
| 83 | 200 | 100 | 200 | 200 | 25 | 25 | 400 | 25 | 50 | 25 | 25 | 25 |
| 85 | 100 | 400 | 100 | 100 | 25 | 500 | 100 | 25 | 200 | 25 | 50 | 25 |
| 86 | 100 | 400 | 100 | 100 | 50 | 25 | 100 | 25 | 50 | 25 | 25 | 25 |
| 87 | 100 | 400 | 100 | 100 | 25 | 50 | 100 | 50 | 25 | 25 | 25 | 25 |
| 88 | 200 | 100 | 400 | 50 | 25 | 50 | 100 | 25 | 400 | 25 | 100 | 50 |
| 90 | 50 | 50 | 25 | 25 | 50 | 25 | 400 | 25 | 200 | 100 | 50 | 50 |
| 94 | 50 | 25 | 50 | 50 | 25 | 100 | 100 | 400 | 50 | 100 | 50 | 50 |
| 96 | 100 | 200 | 100 | 100 | 25 | 25 | 50 | 25 | 50 | 25 | 25 | 50 |
| 100 | 200 | 200 | 100 | 100 | 50 | 25 | 400 | 25 | 100 | 25 | 50 | 50 |
| 101 | 100 | 200 | 50 | 400 | 50 | 25 | 200 | 25 | 50 | 25 | 25 | 25 |
| 103 | 200 | 400 | 400 | 400 | 200 | 25 | 400 | 50 | 100 | 50 | 25 | 50 |
| 105 | 100 | 100 | 50 | 50 | 50 | 25 | 50 | 25 | 25 | 25 | 25 | 25 |
| 106 | 50 | 100 | 50 | 50 | 25 | 25 | 100 | 25 | 25 | 25 | 25 | 25 |
| 107 | 400 | 200 | 100 | 100 | 100 | 25 | 400 | 50 | 100 | 25 | 25 | 50 |
| 108 | 50 | 50 | 50 | 100 | 25 | 25 | 200 | 25 | 25 | 25 | 25 | 25 |
| 109 | 400 | 100 | 100 | 100 | 100 | 25 | 200 | 50 | 200 | 50 | 25 | 25 |
| 110 | 50 | 200 | 100 | 100 | 50 | 50 | 200 | 25 | 100 | 100 | 50 | 50 |
| 115 | 100 | 200 | 200 | 100 | 50 | 25 | 400 | 100 | 200 | 200 | 200 | 100 |
| 125 | 50 | 50 | 50 | 50 | 50 | 25 | 200 | 25 | 100 | 100 | 50 | 25 |
| 135 | 200 | 200 | 200 | 200 | 100 | 50 | 400 | 25 | 200 | 200 | 200 | 200 |
| 141 | 100 | 100 | 100 | 100 | 50 | 25 | 400 | 100 | 100 | 200 | 100 | 100 |
| 183 | 200 | 200 | 200 | 400 | 100 | 25 | 200 | 25 | 25 | 25 | 25 | 25 |

It will be apparent from the above results that the pyrazole compounds (I) in this invention have excellent herbicidal activities and thus they are practically useful as a herbicide for paddy field, upland field, non-crop land and so on.

What is claimed is:

1. An agriculturally compatible compound having the formula wherein
$R_1$ represents hydrogen atom or an alkyl group having from 1 to 3 carbon atoms, $R_2$ represents an alkyl group having from 1 to 3 carbon atoms or an alkenyl group having 3 or 4 carbon atoms, n is an integer of 2 or 3 or 4, Z represents a halogen atom, nitro group, an alkyl group having from 1 to 4 carbon atoms, and when n is 2 or 3 or 4, Z's may be the same or different, and Y represents oxygen atom, and acid addition salts thereof.

2. The compound of claim 1 selected from the group consisting of 1,3-dimethyl-4-(2,4-dichlorobenzoyl)-5-hydroxypyrazole,
1,3-dimethyl-4-(2-nitro-4-chlorobenzoyl)-5-hydroxypyrazole,
1,3-dimethyl-4-(2,5-dichlorobenzoyl)-5-hydroxypyrazole,
1,3-dimethyl-4-(2-chloro-4-nitrobenzoyl)-5-hydroxypyrazole,
1,3-dimethyl-4-(2-nitro-5-methylbenzoyl)-5-hydroxypyrazole,
1,3-dimethyl-4-(2,4-dichlorobenzoyl)-5-hydroxypyrazole hydrochloride, and
1-allyl-3-methyl-4-(2,4-dichlorobenzoyl)-5-hydroxypyrazole.

3. An agriculturally compatible compound having the formula

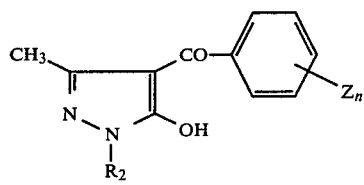

wherein
$R_2$ is methyl or allyl,
Z is methyl, halogen or nitro, and
n is 2 or 3.

* * * * *